United States Patent [19]
Yasohara et al.

[11] Patent Number: 5,654,472
[45] Date of Patent: Aug. 5, 1997

[54] TRIAZOLE DERIVATIVES

[75] Inventors: Yoshihiko Yasohara, Himeji; Kenji Miyamoto, Kobe; Noriyuki Kizaki, Akashi; Shigeru Kawano, Kobe; Junzo Hasegawa, Akashi, all of Japan

[73] Assignee: Kanegafuchi Kagaku Kogyo Kabushiki Kaisha, Osaka, Japan

[21] Appl. No.: 553,558

[22] PCT Filed: Apr. 17, 1995

[86] PCT No.: PCT/JP95/00749

§ 371 Date: Dec. 18, 1995

§ 102(e) Date: Dec. 18, 1995

[87] PCT Pub. No.: WO95/28374

PCT Pub. Date: Oct. 26, 1995

[30] Foreign Application Priority Data

Apr. 19, 1994 [JP] Japan .................................. 6-80741
Apr. 19, 1994 [JP] Japan .................................. 6-80742

[51] Int. Cl.$^6$ .................. C07C 51/36; C07C 69/66; C07C 31/20
[52] U.S. Cl. .................. 560/185; 554/143; 560/263; 562/512.4; 562/590; 562/595

[58] Field of Search ..................... 560/185, 263; 562/512.4, 590, 595; 554/143

[56] References Cited

PUBLICATIONS

"Thymol Derivatives From Schizogyne Glaberrima"—Gonzalez et al, *Phytochemistry*, vol. 25, No. 12, pp. 2889–2891 (1986).

"New Guaianolides From Centipedaminima", Bohlmann et al., *Kexue Tongbao*, vol. 29, No. 7, pp. 900–903 (Jul. 1984).

*Primary Examiner*—Johann Richter
*Assistant Examiner*—Jane C. Oswecki
*Attorney, Agent, or Firm*—Armstrong, Westerman, Hattori, McLeland & Naughton

[57] ABSTRACT

The present invention relates to a novel glycerol derivative and a process for preparing the same, and a process for preparing a triazole derivative.

According to the present invention, an optical active 2-arylglycerol derivative which is a novel and useful as a synthetic intermediate of medicament can be provided and furthermore, (R)-2-(2,4-difluorophenyl)-3-(1H-1,2,4-triazole-1-yl)-propane-1,2-diol which is useful as an antifungal agent can be prepared.

5 Claims, No Drawings

TRIAZOLE DERIVATIVES

This application is a 371 of PCT/JP95/00749 filed Apr. 17, 1995.

TECHNICAL FIELD

The present invention relates to a novel glycerol derivative and a process for preparing the same, and a process for preparing a triazole derivative. More particularly, the invention relates to a novel glycerol derivative, being useful as a raw material for synthesizing a medicament, an agricultural chemical or the like and a process for preparing the same and a process for preparing a triazole derivative.

BACKGROUND ART

Hitherto, a compound useful as a raw material of a medicament or biologically active substance has been variously studied. However, there was no suitable compound from various viewpoint of economy and industry, according to demands for a glycerol derivative and an acetone derivative which can be used as a raw material for synthesizing a medicament, an agricultural chemical or the like. For instance, 1-chloro-2-(2,4-difluorophenyl)-2,3-epoxypropane is synthesized by carrying out ring closure of epoxide using 1,3-dichloro-2-(2,4-difluorophenyl)-2-propanol in the presence of sodium hydride in dimethylformamide, in Japanese Unexamined Patent Publication No. 9183/1993. However, this reaction had problems in industrially carrying out the reaction such as evolution of hydrogen and difficult removal of dimethylformamide after completion of the reaction.

Thus, the compounds which satisfy the various demands such as an 2-aryl-1,3-diacyloxy-2-propanol and a 1,3-diacyloxyacetone being the compounds of the present invention have not been synthesized until now, and there is no existing knowledge as to the preparation thereof. Also, there is no report that the optically active 2-aryl-3-acyloxy-1,2-propanediol represented by the formula (VIII):

has been synthesized or isolated. The above-mentioned compounds of the formula (VIII) including a 2-(2,4-difluorophenyl)-2-acyloxy-1,2-propanediol wherein an aryl group is 2,4-difluorophenyl group are novel compounds, and the industrial process for preparing the same have not been established at present. Further, there is not disclosure as to an optically active compound represented by the formula (IX):

and a process for preparing the same, and thus these compounds are novel compounds. Then, a result of the continuous effort of the present inventors as to a glycerol derivative and an acetone derivative which can be used as a raw material for synthesizing a medicament, a biologically active substance or the like and a process for preparing the same; a novel glycerol derivative, a novel acetone derivative and novel processes for preparing the same have been established. According to the present invention, there can be also easily prepared the optically active 2-aryl-2,3-epoxy-1-propanol being an intermediate for synthesizing a medicament, which was hitherto synthesized by subjecting to cyclization, in the presence of a base, and hydrolysis from an 2-aryl-2-propenol by the of complecated Sharpless epoxidation reaction (ref. the specification of European Patent No. 0539938) and the like. Also, a novel process for preparing a triazole derivative being a compound useful as an intermediate of an antifungal agent (ref. Japanese Unexamined Patent Publication No. 9183/1993 and the specification of European Patent No. 539938). Furthermore, an 2-aryl-1,2,3-propanetriol represented by the formula (III):

is a novel compound, and a process for synthesizing the same is also novel. The present inventors also established processes for preparing those compounds.

The object of the present invention is to provide a novel 1,3-diacyloxyacetone, an optically active 2-arylglycerol derivative which are useful are as a raw material of a medicament or a biologically active substance and processes for preparing them, and a novel process for preparing an intermediate for an existing medicament.

DISCLOSURE OF THE INVENTION

The present invention relates to an 2-aryl-1,3-diacyloxy-2-propanol compound represented by the formula (I):

wherein Ar is an aryl group which may be substituted, R is a normal chain or branched chain alkyl group which may be substituted, a normal chain or branched chain alkenyl group which may be substituted or an aryl group which may be substituted.

Herein, the above compound wherein R is a normal chain or branched chain alkyl group having 1 to 10 carbon atoms, or phenyl group; further the above compound wherein R is methyl, chloromethyl, ethyl, n-propyl, n-butyl, n-pentyl, n-hexyl, n-heptyl, isopropyl, isobutyl, β-chloroethyl or γ-chloropropyl group and the above compound wherein Ar is 2,4-difluorophenyl group are preferable, and the compound wherein Ar is phenyl, 4-fluorophenyl, 4-chlorophenyl, 4-methylphenyl, 4-methoxyphenyl, 4-biphenyl, 4-tert-butylphenyl, 2-chlorophenyl, 2-methylphenyl, 2,4-dichlorphenyl, 2,4-difluorophenyl, 2,4-dimethylphenyl, 1-naphthyl or 2-naphthyl group, R is isopropyl group is more preferable.

Also, the present invention relates to a process for preparing an 2-aryl-1,3-diacyloxy-2-propanol compound represented by the formula (I):

wherein Ar is an aryl group which may be substituted, R is a normal chain or branched chain alkyl group which may be substituted, a normal chain or branched chain alkenyl group which may be substituted or an aryl group which may be substituted, which comprises allowing to react 2,4-difluorophenyllithium,
2,4-difluorophenylmagnesium chloride,
2,4-difluorophenylmagnesium iodide,
2,4-difluorophenylmagnesium bromide,
phenylmagnesium bromide,
4-fluorophenylmagnesium bromide,
4-chlorophenylmagnesium bromide,
4-methylphenylmagnesium bromide,
4-biphenylmagnesium bromide,
4-methoxyphenylmagnesium bromide,
4-tert-butylphenylmagnesium bromide,
2-chlorophenylmagnesium bromide,
2-methylphenylmagnesium bromide,
2,4-dichlorophenylmagnesium iodide,
2,4-dimethylphenylmagnesium bromide,
1-naphthylmagnesium bromide or 2-naphtylmagnesium bromide with a compound represented by the formula (II):

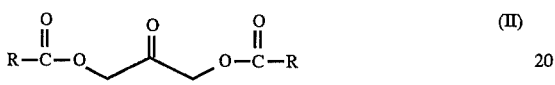

wherein R is the same as the defined above.

Herein, the above process wherein R is a normal chain or branched chain alkyl group having 1 to 10 carbon atoms, or phenyl group; further the above process wherein R is methyl, chloromethyl, ethyl, n-propyl, n-butyl, n-pentyl, n-hexyl, n-heptyl, isopropyl, isobutyl, β-chloroethyl or γ-chloropropyl group; and the process wherein Ar is 2,4-difluorophenyl group are preferable, and the above process wherein Ar is phenyl, 4-fluorophenyl, 4-chlorophenyl, 4-methylphenyl, 4-methoxyphenyl, 4-biphenyl, 4-tert-butylphenyl, 2-chlorophenyl, 2-methylphenyl, 2,4-dichlorophenyl, 2,4-difluorophenyl, 2,4-dimethylphenyl, 1-naphthyl or 2-naphthyl group, R is isopropyl group is more preferable.

Also, the present invention relates to a process for preparing an 2-aryl-1,3-diacyloxy-2-propanol compound represented by the formula (I):

wherein Ar is an aryl group which may be substituted, R is a normal chain or branched chain alkyl group which may be substituted, a normal chain or branched chain alkenyl group which may be substituted or an aryl group which may be substituted, which comprises carrying out position-specifically 1,3-diacylation by allowing to react a compound represented by the formula (IV):

wherein R is the same as the defined above, $X^1$ is a halogen atom, a normal chain or branched chain acyloxy group or a normal chain or branched chain alkoxy group with an aryl-1,2,3-propanol represented by the formula (III):

wherein Ar is the same as the defined above.

Herein, the above process wherein R is a normal chain or branched chain alkyl group having 1 to 10 carbon atoms, or phenyl group, $X^1$ is a halogen atom, a normal chain or branched chain acyloxy group having 1 to 11 carbon atoms or a normal chain or branched chain alkoxy group having 1 to 5 carbon atoms; further the above process wherein R is methyl, chloromethyl, ethyl, n-propyl, n-butyl, n-pentyl, n-hexyl, n-heptyl, isopropyl, isobutyl, β-chloroethyl or γ-chloropropyl group, $X^1$ is acetoxy, chloroacetoxy, propionyloxy, n-butyryloxy, n-pentanoyloxy, n-hexanoyloxy, n-heptanoyloxy, n-octanoyloxy, isobutyryloxy, isopentanoyloxy, β-chloropropionyloxy, γ-chlorobutyryloxy, benzoyloxy, chlorine atom, bromine atom, methoxy, ethoxy, n-propyloxy or isopropyloxy group are preferable.

Also, the present invention relates to a process process for preparing a 1-chloro-2-aryl-2,3-epoxypropane represented by the formula (VI):

wherein Ar is an aryl group which may be substituted, which comprises treating a 1,3-dichloro-2-aryl-2-propanol represented by the formula (V):

wherein Ar is the same as the defined above with a base.

Herein, the above process wherein lithium hydroxide, potassium hydroxide or sodium hydroxide is employed as a base is preferable.

Also, the present invention relates to a process for preparing an 2-aryl-1,3- diacyloxy-2-propanol represented by the formula (I):

wherein Ar is an aryl group which may be substituted, and R is a normal chain or branched chain alkyl group which may be substituted, a normal chain or branched chain alkenyl group which may be substituted or an aryl group which may be substituted, which comprises allowing to react a 1-chloro-2-aryl-2,3-epoxypropane represented by the formula (VI):

wherein Ar is the same as the defined above with a carboxylic acid represented by the formula (VII):

wherein R is the same as the defined above and its salt.

Herein, the above process wherein R is a normal chain or branched chain alkyl group having 1 to 10 carbon atoms, or phenyl group; further the above process wherein R is methyl, chloromethyl, ethyl, n-propyl, n-butyl, n-pentyl, n-hexyl, n-heptyl, isopropyl, isobutyl, β-chloroethyl or γ-chloropropyl group; and the above process wherein a salt of carboxylic acid is an alkali metal salt, an alkaline earth metal salt or an amine salt of carboxylic acid; further the above process wherein a salt of carboxylic acid is lithium salt, sodium salt, potassium salt, magnesium salt, calcium salt, ammonium salt, trimethylammonium salt, triethylammonium salt, tetramethylammonium salt or tetraethylammonium salt of carboxylic acid are preferable.

Also, the present invention relates to a 1,3-diacyloxyacetone compound represented by the formula (II):

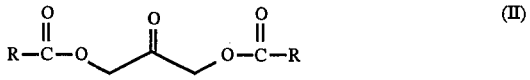

wherein R is a normal chain or branched chain alkyl group which may be substituted, a normal chain or branched chain alkenyl group which may be substituted or an aryl group which may be substituted.

Herein, the compound of the above 1,3-diacyloxyacetone wherein R is a normal chain or branched chain alkyl group having 1 to 10 carbon atoms; further the above compound of the 1,3-diacyloxyacetone wherein R is ethyl, n-butyl, n-hexyl, isopropyl, isobutyl, chloromethyl, β-chloroethyl or γ-chloropropyl group are preferable.

Also, the present invention relates to a process for preparing a 1, 3-diacyloxyacetone represented by the formula (II):

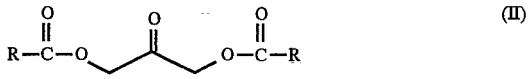

wherein R is a normal chain or branched chain alkyl group which may be substituted or a normal chain or branched chain alkenyl group which may be substituted or an aryl group which may be substituted, which comprises allowing to react 1,3-dihydroxyacetone with a compound represented by the formula (IV):

wherein R is the same as the defined above, $X^1$ is a halogen, a normal chain or branched chain acyloxy group or a normal chain or branched chain alkoxy group.

Herein, the above process wherein R is a normal chain or branched chain alkyl group having 1 to 10 carbon atoms, $X^1$ is a halogen or a normal chain or branched chain acyloxy group having 1 to 11 carbon atoms; further the compound of claim 24 wherein R is chloromethyl, ethyl, n-butyl, n-hexyl, isopropyl, isobutyl, β-chloroethyl or γ-chloropropyl, $X^1$ is chloroacetoxy, propionyloxy, n-pentanoyloxy, n-heptanoyloxy, isobutyryloxy, isopentanoyloxy, β-chloropropionyloxy, γ-chloro-butyryloxy, chlorine atom or bromine atom are preferable.

Also, the present invention relates to an optically active 2-aryl-3-acyloxy-1,2-propanediol compound represented by the formula (VIII):

wherein Ar is an aryl group which may be substituted, R is a normal chain or branched chain alkyl group which may be substituted, a normal chain or branched chain alkenyl group which may be substituted or an aryl group which may be substituted.

Herein, the above compound represented by the formula (VIIIa):

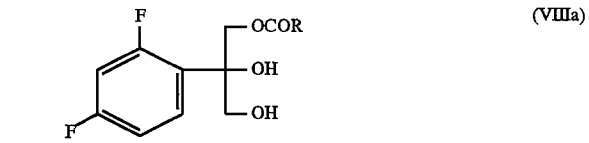

wherein Ar is 2,4-difluorophenyl group, R is a normal chain or branched chain alkyl group, or phenyl group; further the compound wherein R is methyl, ethyl, n-propyl, n-butyl, n-pentyl, n-hexyl, n-heptyl, isopropyl, isobutyl, chloromethyl, β-chloroethyl or γ-chloropropyl group; and the compound represented by the formula (VIIIb):

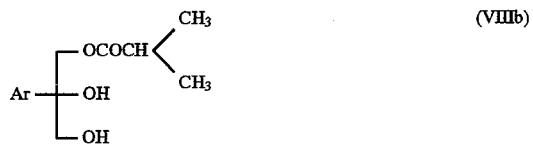

wherein Ar is an aryl group which may be substituted wherein R is isopropyl group; further the compound wherein Ar is phenyl, 4-fluorophenyl, 4-chlorophenyl, 4-methylphenyl, 4-methoxyphenyl, 4-biphenyl, 4-tert-butylphenyl, 2-chlorophenyl, 2-methylphenyl, 2,4-dichlorophenyl, 2,4-difluorophenyl, 2,4-dimethylphenyl, 1-naphthyl or 2-naphthyl group are preferable.

Also, the present invention relate to a process for preparing an optically active 2-aryl-3-acyloxy-1,2-propanediol, which comprises allowing to act a microorganism or an enzyme having enzyme activity which allow to form an optically active 2-aryl-3-acyloxy-1,2-propanediol represented by the formula (VIII):

wherein Ar is an aryl group which may be substituted, R is a normal chain or branched chain alkyl group, a normal chain or branched chain alkenyl group which may be substituted or an aryl group which may be substituted by stereospecific hydrolysis of an 2-aryl-1,3-diacyloxy-2-propanol represented by the formula (I):

wherein each of Ar and R is the same as each of the defined above, on an 2-aryl-1,3-diacyloxy-2-propanol represented by the formula (I) and allowing to form an optically active 2-aryl-3-acyloxy-1,2-propanediol represented by the formula (VIII).

Herein, the above process wherein Ar is 2,4-difluorophenyl group, R is a normal chain or branched chain alkyl group, or phenyl group; further the above process wherein R is methyl, ethyl, n-propyl, n-butyl, n-pentyl, n-hexyl, n-heptyl, isopropyl, isobutyl, chloromethyl, β-chloroethyl or γ-chloropropyl group are preferable, and the above process wherein R is isopropyl group and the above process wherein Ar is phenyl, 4-fluorophenyl, 4-chlorophenyl, 4-methylphenyl, 4-methoxyphenyl, 4-biphenyl, 4-tert-butylphenyl, 2-chlorophenyl, 2-methylphenyl, 2,4-dichlorophenyl, 2,4-difluorophenyl, 2,4-dimethylphenyl, 1-naphthyl or 2-naphthyl group are more preferable.

Additionally, the above process wherein the microorganism or enzyme which hydrolyzes stereospecifically is a member selected from the group consisting of the microorganism belonging to Chromobacterium genus, Rhizopus genus, Mucor genus, Candida genus, Aspergillus genus, Geotrichum genus, Pseudomonas genus, Bacillus genus or Humicola genus, the enzyme derived from that microorganism and the enzyme derived from porcine pancreas; the above process wherein the stereospecific hydrolysis is carried out in the presence of an organic solvent; the process wherein the stereospecific hydrolysis is carried out at 15° C. or below; and the above process wherein the stereospecific hydrolysis is carried out at pH 6 or below are preferable, and further the above process wherein the organic solvent is a hydrocarbon is preferable.

Also, the present invention relates to a process for preparing an optically active 2-aryl-3-acyloxy-1,2-propanediol, which comprises allowing to act a microorganism or an enzyme having enzyme activity which esterifies only hydroxy group at 1-position or 3-position stereospecifically on an 2-aryl-1,2,3-propanetriol represented by the formula (III):

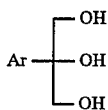
(III)

wherein Ar is an aryl group which may be substituted in the presence of an acylating agent and allowing to form an optically active 2-aryl-3-acyloxy-1,2-propanediol represented by the formula (VIII):

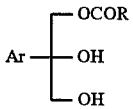
(VIII)

wherein Ar is the same as the defined above, R is a normal chain or branched chain alkyl group which may be substituted, a normal chain or branched chain alkenyl group which may be substituted or an aryl group which may be substituted.

Herein, the above process wherein Ar is 2,4-difluorophenyl group, R is a normal chain or branched chain alkyl group, or phenyl group; the above process wherein the acylating agent is carboxylic acid, a carboxylic acid ester or a carboxylic acid anhydride; and the above process wherein the microorganisms or enzyme which esterifies stereospecifically is a member selected from the group consisting of the microorganism belonging to Chromobacterium genus, Rhizopus genus, Mucor genus, Candida genus, Aspergillus genus, Geotrichum genus, Pseudomonas genus, Bacillus genus or Humicola genus, the enzyme derived from that microorganism, the enzyme derived from porcine pancreas and the enzyme derived from wheat are preferable, further the above process wherein R is methyl, ethyl, n-propyl, n-butyl, n-pentyl, n-hexyl, n-heptyl, isopropyl, isobutyl, chloromethyl, β-chloroethyl or γ-chloropropyl group is preferable.

Also, the present invention relates to an optically active compound represented by the formula (IX):

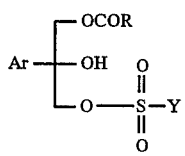
(IX)

wherein Ar is an aryl group which may be substituted, R is a normal chain or branched chain alkyl group which may be substituted, a normal chain or branched chain alkenyl group which may be substituted or an aryl group which may be substituted, Y is a lower alkyl group which may be substituted, a phenyl group or a benzyl group which may be substituted.

Herein, the above compound represented by the formula (IXa):

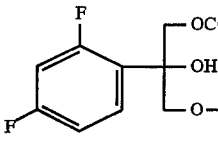
(IXa)

wherein Ar is 2,4-difluorophenyl group, R is a normal chain or branched chain alkyl group, Y is methyl, ethyl, trifluoromethyl, phenyl, p-methylphenyl or benzyl group; further the compound wherein R is methyl, ethyl, n-propyl, isopropyl or n-butyl group, Y is methyl or p-methylphenyl group are preferable, and the above compound wherein R is methyl group, Y is methyl group; and the above compound wherein R is isopropyl group, Y is methyl group are more preferable.

Also, the present invention relates to an optically active compound represented by the formula (IX):

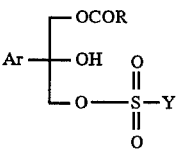
(IX)

wherein Ar is an aryl group which may be substituted, R is a normal chain or branched chain alkyl group which may be substituted, a normal chain or branched chain alkenyl group which may be substituted or an aryl group which may be substituted, Y is a lower alkyl group which may be substituted, a phenyl group or a benzyl group which may be substituted by allowing to act sulfonic acid halide represented by the formula (X):

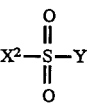
(X)

wherein Y is the same as the defined above, $X^2$ is a halogen atom on an optically active 2-aryl-3-acyloxy-1,2-propanediol represented by the formula (VIII):

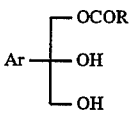
(VIII)

wherein Ar is the same as the defined above.

Herein, the the above process wherein Ar is 2,4-difluorophenyl group, R is a normal chain or branched chain alkyl group in the optically active 2-aryl-3-acyloxy-1,2- propanediol represented by the formula (VIII), and Y is methyl, ethyl, trifluoromethyl, phenyl, p-methylphenyl or benzyl group, $X^2$ is a halogen atom in the sulfonic acid halide represented by the formula (X); further the above process wherein methanesulfonyl chloride is allowed to act on an optically active 2-(2,4-difluorophenyl)-1-acetoxy-2,3-propanediol to prepare optically active 2-(2,4-difluorophenyl)-1-acetoxy-3-methanesulfonyloxy-2-propanol; and the above process wherein methanesulfonyl chloride allowed to act on optically active 2-(2,4-difluorophenyl)-1-isobutyryloxy-2,3-propanediol to prepare optically active 2-(2,4-difluorophenyl)-1-isobutyryloxy-3-methanesulfonyloxy-2-propanol are preferable.

Also, the present invention relates to a process for preparing an optically active 2-aryl-2,3-epoxy-1-propanol represented by the formula (XI):

wherein Ar is an aryl group which may be substituted, which comprises carrying out, in the presence of a base, cyclization and further hydrolysis of ester of an optically active compound represented by the formula (IX):

wherein Ar is the same as the defined above, R is a normal chain or branched chain alkyl group which may be substituted, a normal chain or branched chain alkenyl group which may be substituted or an aryl group which may be substituted, Y is a lower alkyl group which may be substituted, a phenyl group or a benzyl group which may be substituted.

Herein, the above process, which comprises allowing to cyclize an optically active 2-(2,4-difluorophenyl)-1-acetoxy-3-methanesulfonyloxy-2-propanol and further to carry out hydrolysis of ester in the presence of a base to prepare an optically active 2-(2,4-difluophenyl)-2,3-epoxy-1-propanol represented by the formula (XIa):

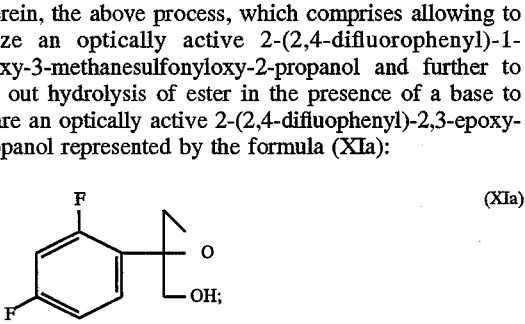

and the above process, which comprises allowing to cyclize optically active 2-(2,4-difluoro-phenyl)-1-isobutyloxy-3-methanesulfonyloxy-2-propanol and further carrying out to hydrolyze ester in the presence of a base to prepare optically active 2(2,4-difluorophenyl)-2,3-epoxy-1-propanol represented by the formula (XIa):

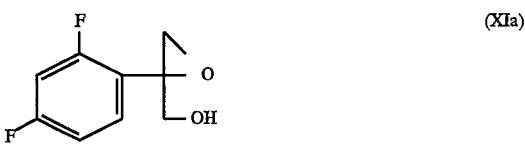

are preferable.

Also, the present invention relates to a process for preparing an optically active 2-aryl-3-triazole-1,2-propanediol represented by the formula (XII):

wherein Ar is an aryl group which may be substituted, which comprises allowing to act triazole on an optically active compound represented by the formula (IX):

wherein Ar is the same as the defined above, R is a normal chain or branched chain alkyl group which my be substituted, a normal chain or branched chain alkenyl group which may be substituted or an aryl group which may be substituted, Y is a lower alkyl group which may be substituted, a phenyl grup or a benzyl group which may be substituted and further carrying out to hydrolyze ester in the presence of a base and an an 2-aryl-1,2,3-propanetriol represented by the formula (III):

wherein Ar is an aryl group which may be substituted. Herein, the above compound wherein the compound is 2-(2,4-difluorophenyl)-1,2,3-propanetriol represented by the formula (IIIa):

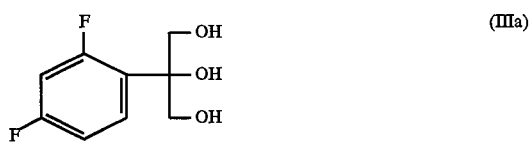

is preferable.

Also, the present invention relates to a process for preparing an 2-aryl-1,2,3-propanetriol, which comprises hydrolyzing an 2-aryl-1,3-diacyloxy-2-propanol represented by the formula (I):

wherein Ar is an aryl group which may be substituted R is a normal chain or branched chain alkyl group which may be substituted, a normal chain or branched chain alkenyl group which may be substituted or an aryl group which may be substituted or a compound represented by the formula (VIII):

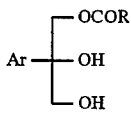

wherein each of Ar and R is the same as each of the defined above and allowing to act an enzyme having enzyme activity which allow to form 2-aryl-1,2,3-propanetriol represented by the formula (III):

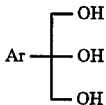

wherein Ar is the same as the defined above on a compound represented by the formula (VIII) or (I) to form 2-aryl-1,2,3-propanetriol and a process for preparing an 2-aryl-1,2,3-propanetriol, which comprises hydrolyzing an 2-aryl-1,3-diacyloxy-2-propanol represented by the formula (I):

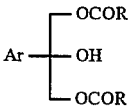

wherein Ar is an aryl group which may be substituted, R is a normal chain or branched chain alkyl group which may be substituted, a normal chain or branched chain alkenyl group which may be substituted or an aryl group which may be substituted, or an 2-aryl-3-acyloxy-1,2-propanediol represented by the formula (VIII):

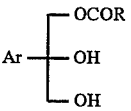

wherein each of Ar and R is the same as each of the defined above in the presence of a base to form an 2-aryl-1,2,3-propanetriol represented by the formula (III):

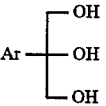

wherein Ar is the same as the defined above.

Examples of an aryl group represented by Ar in each compound of formulae (I), (II), (III), (IV), (V), (VI), (VII), (VIII), (IX), (X), (XI) and (XII), which may be substituted, in the present invention, are 2,4-difluorophenyl, phenyl, 4-fluorophenyl, 4-chlorophenyl, 4-methylphenyl, 4-methoxyphenyl, 4-biphenyl, 4-tert-butylphenyl, 2-chlorophenyl, 2-methylphenyl, 2,4-dichlorophenyl, 2,4-dimethylphenyl, 1-naphthyl and 2-naphthyl group and particularly 2,4-difluorophenyl group is preferable.

Examples of a normal chain or branched chain alkyl group which may be substituted, a normal chain or branched chain alkenyl group which may be substituted or an aryl group which may be substituted, represented by R, are preferably a normal chain or branched chain alkyl group having 1 to 10 carbon atoms, or phenyl group and particularly methyl, ethyl, n-propyl, n-butyl, n-pentyl, n-hexyl, n-heptyl, isopropyl, isobutyl, chloromethyl, β-chloroethyl and γ-chloropropyl group are preferable and isopropyl group is more preferable.

Examples of a lower alkyl group which may be substituted, a phenyl group or a benzyl group which may be substituted represented by Y, are methy, ethyl and trifluoromethyl group; phenyl, p-methylphenyl, benzyl and 2,4-dinitrophenyl group; respectively. Particularly, methyl, ethyl, trifluoromethyl, phenyl, p-methylphenyl and benzyl group and preferable.

Examples of a halogen atom, a normal chain or branched chain acyloxy group or a normal chain or branched chain alkoxy group represented $X^1$, are a halogen atom; a normal chain or branched chain acyloxy group having 1 to 11 carbon atoms; and a normal chain or branched chain alkoxy group having 1 to 5 carbon atoms, respectively and particularly chlorine atom, bromine atom; acetoxy, chloroacetoxy, propionyloxy, n-butyryloxy, n-pentanoyloxy, n-hexanoyloxy, n-heptanoyloxy, n-octanoyloxy, isobutyryloxy, isopentanoyloxy, β-chloropropionyloxy, γ-chlorobutyryloxy, benzoyloxy; and methoxy, ethoxy, n-propyloxy or isopropyloxy group, respectively are more preferable.

Examples of a halogen atom represented by $X^2$ are chlorine atom, bromine atom, fluorine atom and iodine atom.

Preferable examples of the 2-aryl-1,3-diacyloxy-2-propanol in the present invention represented by the formula (I):

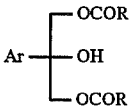

wherein Ar is the same as the defined above, are particularly 2-phenyl-1,3-diisobutyryloxy-2-propanol,
2-(4-fluorophenyl)-1,3-diisobutyryloxy-2-propanol,
2-(4-chlorophenyl)-1,3-diisobutyryloxy-2-propanol,
2-(4-methylphenyl)-1,3-diisobutyryloxy-2-propanol,
2-(4-methoxyphenyl)-1,3-diisobutyryloxy-2-propanol,
2-(4-biphenyl)-1,3-diisobutyryloxy-2-propanol,
2-(4-tert-butylphenyl)-1,3-diisobutyryloxy-2-propanol,
2-(2-chlorophenyl)-1,3-diisobutyryloxy-2-propanol,
2-(2-methylphenyl)-1,3-diisobutyryloxy-2-propanol,
2-(2,4-difluorophenyl)-1,3-diisobutyryloxy-2-propanol,
2-(2,4-dichlorophenyl)-1,3-diisobutyryloxy-2-propanol,
2-(2,4-dimethylphenyl)-1,3-diisobutyryloxy-2-propanol,
2-(1-naphthyl)-1,3-diisobutyryloxy-2-propanol,
and 2-(2-naphtyl)-1,3-diisobutyryloxy-2-propanol.

Preferable examples of the 1,3-diacyloxyacetone in the present invention represented by the formula (II):

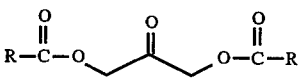

wherein R is the same as the defined above, are particularly, 1,3-diacetoxyacetone, 1,3-dipropionyloxyacetone, 1,3-di-n-butyryloxyacetone and 1,3-diisobutyryloxyacetone.

Those compounds are useful compounds as a raw material of various medicaments or biologically active substances.

By the following three kinds of processes for preparation is synthesized 2-aryl-1,3-diacyloxy-2-propanol represented by the formula (I).

In the first process (shown in the following Reaction formula 1):

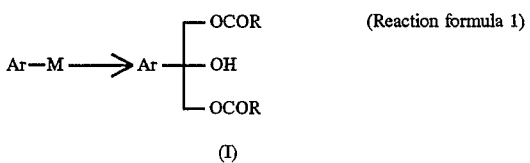

(Reaction formula 1)

(I)

wherein each Ar and R is the same as each of the defined above, M is Li, MgCl, MgBr or MgI, the 2-aryl-1,3-diacyloxy-2-propanol is obtained by allowing to react an organic metal compound such as 2,4-difluorophenyllithium, 2,4-difluorophenylmagnesium chloride, 2,4-difluorophenylmagnesium iodide, 2,4-difluorophenylmagnesium bromide, phenylmagnesium bromide, 4-fluorophenylmagnesium bromide, 4-chlorophenylmagnesium bromide, 4-methylphenylmagnesium bromide, 4-biphenylmagnesium bromide, 4-methoxyphenylmagnesium bromide, 4-tert-butylphenylmagnesium bromide, 2-chlorophenylmagnesium bromide, 2-methylphenylmagnesium bromide, 2,4-dichlorophenylmagnesium iodide, 2,4-dimethylphenylmagnesium bromide, 1-naphthylmagnesium bromide or 2-naphtylmagnesium bromide with 1,3-diacyloxyacetone represented by the formula (n):

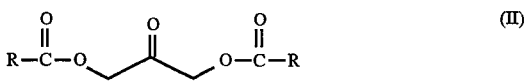

(II)

wherein R is the same as the defined above.

The 2, 4-difluorophenyllithium employed in the present invention can be prepared by treating 2,4-difluorobromobenzene, 2,4-difluorochlorobenzene or 2,4-difluoroiodobenzene with a base such as n-butyl lithium. Also, 2,4-difluorophenylmagnesium bromide, 2,4-difluorophenylmagnesium chloride, 2,4-difluorophenylmagnesium iodide, phenylmagnesium bromide, 4-fluorophenylmagnesium bromide, 4-chlorophenylmagnesium bromide, 4-methylphenylmagnesium bromide, 4-biphenylmagnesium bromide, 4-methoxyphenylmagnesium bromide, 4-tert-butylphenylmagnesium bromide, 2-chlorophenylmagnesium bromide, 2-methylphenylmagnesium bromide, 2,4-dichlorophenylmagnesium iodide, 2,4-dimethylphenylmagnesium bromide, 1-naphthylmagnesium bromide or 2-naphtylmagnesium bromide employed in the present invention can be prepared by allowing to react 2,4-difluorobromobenzene, 2,4-difluorochlorobenzene, 2,4-difluoroiodobenzene, bromobenzene, 4-fluorobromobenzene, 4-chlorobromobenzene, 4-bromotoluene, 4-bromobipheny, 4-bromoanisole, 1-bromo-4-tert-butylbenzene, 2-chlorobromobenzene, 2-bromotoluene, 2,4-dichloroiodobenzene, 4-bromo-m-xylene, 1-bromonaphthalene and 2-bromonaphthalene, respectively with metal magnesium.

The preferable solvents employed in the process of the present invention are usually ether solvents such as diethylether and THF. Alternatively, the solvent may be used by mixing a solvent which is inactive against a reaction for example, a reaction employing hexane, with the above solvent. The reaction according to the present invention is carried out at a temperature of −80° to reflux temperature of the solvent. In order to avoid decomposing a raw material or product, it is preferably carried out at −30° C. or below.

The amount of 1,3-diacyloxyacetone (II) is a range of 1 to 1.2 equivalents to that of an organic metal compound. After the reaction is finished, the reaction mixture was added in an acid aqueous solution under ice cooling with keeping pH accescence and then, the resulting liquid was extracted with an organic solvent such as ethyl acetate to give the desired product readily.

As to process the for preparing 1,3-diacyloxyacetone (II), 1,3-diacyloxyacetone is obtained by allowing to react dihydroxyacetone monomer or dimer in the presence of a base with acid anhydride or acid halide. The reaction can be carried out without a solvent but it is preferable to employ organic solvents such as halogenated hydrocarbon, for example, methylene chloride, chloroform, carbon tetrachloride and the like, or aromatic hydrocarbons, for example, benzene, toluene, xylene and the like. To the reaction liquid, 2 or more equivalents of base to that of dihydroxyacetone dimer may be added. Examples of the bases are tertiary amines such as triethylamine, trimethylamine, diisopropylethylamine, N,N-dimethylaniline and N,N-diethylaniline; aromatic nitrogen compounds such as pyridine, 4-(N,N-dimethylamino)pyridine, imidazole, 2,6-lutidine, sodium hydride and potassium hydride. The reaction temperature can be employed at broad temperature range and usually a temperature of −10° C. to a reflux temperature of the solvent is employed. After the reaction is finished, to the resulting liquid is added a water which contains a base such as acid, alkali or ammonium chloride with keeping pH of the reaction liquid around neutral. And then, the resulting liquid is extracted with an organic solvent such as ethyl acetate to give the desired product readily.

As to the process for preparing 1,3-diacetoxyacetone, a process wherein 1,3-diacetoxyacetone is synthesized by employing dihydroxyacetone dimer, and acetyl chloride or acetic acid anhydride is known (ref. the reference by Hiroshi Suemune, Chemical Pharmaceutical Bulletin, 34(8), 3440 (1986)).

According to the second process (shown in the following Reaction formula 2):

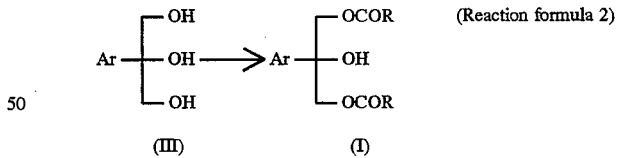

(III)　　(I)

the 2-aryl-1,3-diacyloxy-2-propanol represented by the formula (I):

(I)

wherein Ar is an aryl group which may be substituted, R is a normal chain or branched chain alkyl group which may be substituted, a normal chain or branched chain alkenyl group which may be substituted or an aryl group which may be substituted is obtained by carring out position-specifically 1,3-diacylation by allowing to react an acid halide, an acid anhydride or an ester represented by the formula (IV):

 (IV)

wherein R is the same as the defined above, $X^1$ is a halogen atom, a normal chain or branched chain acyloxy group or a normal chain or branched chain alkoxy group with an aryl-1,2,3-propanetriol represented by the formula (III):

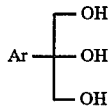 (III)

wherein Ar is the same as the defined above.

In the above reaction, 2 or more equivalents of compound represented by the formula (IV) to that of compound of the formula (III) may be employed. In case the acid halide or the acid anhydride is employed, if necessary, to the reaction liquid may be added a tertiary amine such as triethylamine, trimethylamine, diisopropylethlyamine, N,N-dimethylaniline N,N-diethylaniline; and an aromatic nitrogen compound such as pyridine, imidazole or 2,6-butidine; or sodium methoxide, sodium ethoxide, sodium hydride or potassium hydride. In case the ester is employed, if necessary, to the reaction liquid may be added hydrochloric acid, sulfuric acid or phosphoric acid as an acid catalyst and while may be added sodium methoxide, sodium ethoxide, sodium hydride or potassium hydride as an alkali catalyst. The above reaction can be carried out without a solvent but it is preferable to carry it out in an organic solvent such as halogenated hydrocarbon, for example, methylene chloride, chloroform or carbon tetrachloride; aromatic hydrocarbon, for example, benzene, toluene or xylene; or dimethylformamide. The reaction temperature can be employed at broad temperature range and usually a temperature of –10° to –40° C. is employed in order to carry out position-specifically 1,3-diacylation because acylation of hydroxyl group at 2-position occurs at high temperature. After the reaction is finished, to the resulting liquid is added a water which contains an acid, an alkali or a base such as ammonium chloride with keeping pH of the reaction liquid around neutral. And then, the resulting liquid is extracted with an organic solvent such as ethyl acetate to give the desired product readily.

According to the third process (shown in the following Reaction formula 3):

(Reaction formula 3)

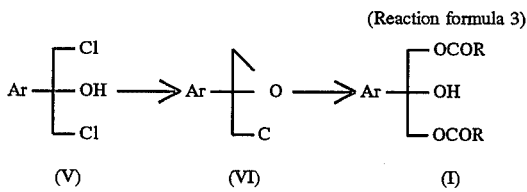

the 2-aryl-1,3-diacyloxy-2-propanol represented by the formula (I):

 (I)

wherein Ar is an aryl group which may be substituted, and R is a normal chain or branched chain alkyl group which may be substituted, a normal chain or branched chain alkenyl group which may be substituted or an aryl group which may be substituted is obtained by allowing to react a 1-chloro-2-arylphenyl-2,3-epoxypropane represented by the formula (VI):

 (VI)

wherein Ar is the same as the defined above with a carboxylic acid represented by the formula (VII):

RCOOH (VII)

wherein R is the same as the defined above and its salt.

The 1,3-dichloro-2-aryl-2-propanol (IV) being the raw material of the above reaction, for example, in case of 1,3-dichloro-2-(2,4-difluorophenyl)-2-propanol, is obtained by allowing to react 2,4-difluorobromobenzene with 1,3-dichloroacetone in an organic solvent such as anhydrous ether or hexane at the presence of a base such as n-butyllithium, according to the known process by references (ref., for example, Japanese Unexamined Patent Publication No. 32868/1983).

The above 1-chloro-2-aryl-2,3-epoxypropane (VI) is obtained by resolving 1,3-dichloro-2-aryl-2-propanol (V) in a halogenated hydrocarbon such as methylene chloride, chloroform or carbon tetrachloride; or an aromatic hydrocarbon such as benzene, toluene or xylene, and then, thereto is added an aqueous solution which contains 1 or more equivalents basic substance such as lithium hydroxide, sodium hydroxide or potassium hydroxide, to that of compound (V) to be allowed to react in two phase. Also, an after-treatment may be only separation of organic layer from water layer.

The above 2-aryl-1,3-diacyloxy-2-propanol of the formula (I) is obtained by allowing to react 1-chloro-2-(2,4-difluorophenyl)-2,3-epoxypropane (VI) with a carboxylic acid of the formula (VII) and its salt. The amount of the above carboxylic acid is 5 or more equivalents to that of compound (VI) and preferably 2 to 5 equivalents to that of compound (VI).

The reaction temperature can be employed at broad temperature range. In order to raise reaction rates, the temperature is employed at 80° C. or more, and preferable at 100° C. or more. After the reaction is finished, the resulting reaction liquid is distilled under reduced pressure to remove carboxylic acid or to the resulting reaction liquid wherein acid is neutralized is added water and then the liquid is extracted with the organic solvent.

It is preferable that a salt of carboxylic acid is an alkali metal salt, and alkaline earth metal salt or an amine salt of carboxylic acid and more preferable that the salt of carboxylic acid is lithium salt, sodium salt, potassium salt, magnesium salt, calcium salt, ammonium salt, trimethylammonium salt, triethylammonium salt, tetramethylammonium salt or tetraethylammonium salt of carboxylic acid.

As a result of further vigorous effort by the present inventors on examination of a process for preparing an optically active 2-arylglycerol derivative, a presence of microorganism and enzyme having an enzymatic activity which hydrolyzes stereospecifically the 2-aryl-1,3-diacyloxy-2-propanol represented by the formula (I) to form the optically active 2-aryl-3-acyloxy-1,2-propanediol represented by the formula (VIII), and an enzymatic activity which esterifies stereospecifically only one side hydroxyl group at 1-position or at 3-position of 2-aryl-1,2,3-propanetriol represented by the formula (III) in the presence of an acylating agent, has been found.

The industrial process for preparing the optically active 2-aryl-3-acyloxy-1,2-propanediol which includes the compound represented by the formula (VIII), being useful as an intermediate of a medicament has been estabilished by the present invention.

That is, the compound represented by the formula (VIII) is synthesized by allowing to act a microorganism or an enzyme having enzymatic activity which allow to form the optically active 2-aryl-3-acyloxy-1,2-propanediol represented by the formula (VIII) by stereospecific hydrolysis of the 2-aryl-1,3-diacyloxy-2-propanol represented by the formula (I):

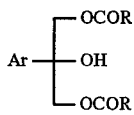

(I)

optically active 2-aryl-3-acyloxy-1,2-propanediol represented by the formula (VIII). Those microorganisms, animal tissues and enzymes having the above activity can be searched by the method shown in the following Example 28. The concrete examples of the microorganisms or enzymes are Chromobacterium genus, Rhizopus genus, Mucor genus, Candida genus, Aspergillus genus, Geotrichum genus, Pseudomonas genus, Bacillus genus and Humicola genus, and the enzymes derived from those microorganisms, the enzymes derived from mammalian viscera, and more detail, are *Chromobacterium viscosum, Rhizopus delemar, Rhizopus javanicus, Mucor jananicus, Candida antarctica, Aspergillus niger, Geotrichum candidum, Pseudomonas fluorescens, Bacillus sp., Humicola sp.* and the enzymes derived from porcine panceas.

The commercially available enzymes thereof are shown in Tables 1 and 2. The enzymes may be employed in accordance with whether a form of the desired compound is R-form or S-form.

TABLE 1

| Enzyme No. | Enzyme name | Origin | Manufacturer |
|---|---|---|---|
| 1 | Lipase | Porcine pancreas | Wako Pure Chemical Industries, Ltd. |
| 2 | Lipase | *Chromobacterium viscosum* | Asahi Chemical Industry Co., Ltd. |
| 3 | Lipase | *Rhizopus delemar* | SEIKAGAKU CORPORATION |
| 4 | Lipase Saiken 50 | *Rhizopus javanicus* | Osaka Bacterial Research Institute |
| 5 | Lipase Saiken 100 | *Rhizopus javanicus* | Osaka Bacterial Research Institute |
| 6 | Lipase D | *Rhizopus delemar* | Amano Pharmaceutical Co., Ltd. |
| 7 | Lipase | *Mucor javanicus* | BIOCATALYSIS, Ltd. |
| 8 | Suizousei-shoukakouso | | Amano Pharmaceutical Co., Ltd. |
| 9 | Serureisu | | Nagase & Co., Ltd. |
| 10 | SP 526 | *Candida antarctica* | NOVO NORDISK, Ltd. |

TABLE 2

| Enzyme No. | Enzyme name | Origin | Manufacturer |
|---|---|---|---|
| 11 | Lipase AP4 | *Aspergillus niger* | Amano Pharmaceutical Co., Ltd. |
| 12 | Lipase AP6 | *Aspergillus niger* | Amano Pharmaceutical Co., Ltd. |
| 13 | Lipase MAP10 | *Mucor javanicus* | Amano Pharmaceutical Co., Ltd. |
| 14 | Lipase MY | *Candida cylindracea* | Meito Industries, Ltd. |
| 15 | Lipase FAP15 | *Rhizopus javanicus* | Amano Pharmaceutical Co., Ltd. |
| 16 | Lipase PS | *Pseudomonas fluorescens* | Amano Pharmaceutical Co., Ltd. |
| 17 | Lipase GC | *Geotrichum candidum* | Amano Pharmaceutical Co., Ltd. |
| 18 | Talipase | *Rhizopus delemer* | Tanabe Seiyaku Co., Ltd. |
| 19 | SP 388 | *Mucor meihei* | NOVO NORDISK, Ltd. |
| 20 | SP 523 | *Humicola sp.* | NOVO NORDISK, Ltd. |
| 21 | SP 524 | *Mucor meihei* | NOVO NORDISK, Ltd. |
| 22 | SP 525 | *Candida antarctica* | NOVO NORDISK, Ltd. |
| 23 | SP 539 | *Bacillus sp.* | NOVO NORDISK, Ltd. |
| 24 | Novozym 435 | *Candida antarctica* | NOVO NORDISK, Ltd. |
| 25 | Lipozym IM | *Mucor meihei* | NOVO NORDISK, Ltd. |
| 26 | Subtilisin A | *Bacillus subtilis* | NOVO NORDISK, Ltd. | wherein each of Ar and R is the same as each of the defined above, on the 2-aryl-1,3-diacyloxy-2-propanol represented by the formula (I).

Examples of microorganisms or enzymes employed in the present invention can be any microorganism, animal tissue or enzyme which is separated therefrom, which has activity that stereospecifically hydrorizes the 2-aryl-1,3-diacyloxy-2-propanol represented by the formula (I) to form the In the process for preparing the optically active compound represented by the formula (VIII) by carrying out stereospecifically hydrolysis of the substrate represented by the formula (I), the hydrolysis reaction is carried out the following steps. The substrate is suspended in water or buffer in a preferable range of 0.1% to 90% (w/v) and then, suitable enzyme, for example at a range of 1:1 to 500:1 (weight ratio of substrate and enzyme) is added to the resulting suspension with stirring at a temperature of 10° to 45° C., preferable 5° to 15° C. In case of alkaline condition, a main constituent is readily racemized and the optical purity thereof falls, therefore, the pH is preferably in a range of 3 to 6. Alternatively, according to a progress of the hydrolysis, pH of the reaction liquid tends to towards acidic side, therefore, the pH may be kept by suitable alkaline solution such as sodium hydroxide. Further, in order to stimulate a progress of the reaction, the organic solvents which do not inhibit the enzyme reaction may be optionally added to the reaction liquid. Examples of the solvents are n-hexane, cyclohexane, methylcyclohexane, n-heptane, n-octane, isooctane, n-decane, benzene, toluene, chloroform, petroleum ether and diisopropyl ether and more preferably is hydrocarbon. Also, the enzymes can be used by immobilizing on suitable water-insoluble carries such as ion-exchange resin.

After the hydrolysis, in order to isolate an 2-aryl-3-acyloxy-1,2-propanediol, being product from the reaction liquid, the general isolation method can be employed. For example, extraction is carried out by addition an organic solvent such as ethyl acetate to the reaction liquid. After the resulting liquid is dried, the organic solvent is removed under reduced pressure. As the result, the optically active 2-aryl-3-acyloxy-1,2-propanediol can be obtained. Furthermore, it can be purified in high purity by purification procedures such as crystallization, distillation and column chromatography on silica gel.

The optically active compound represented by the formula (VIII) is synthesized by allowing to act a microorganism or an enzyme having enzymatic activity which esterifies only hydroxyl group at 1-position or at 3-position stereospecifically on an 2-aryl-1,2,3-propanetriol represented by the formula (III):

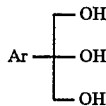 (III)

wherein Ar is the same as the defined above and acylating agent.

The process for preparing the 2-aryl-1,2,3-propanetriol represented by the formula (III) being a raw material in the process of the present invention is described later.

Examples of enzymes used in the present invention can be employed any microorganism, animal tissue or enzyme which is separated therefrom, which has activity that esterifies stereospecifically only hydroxyl group at 1-position or 3-position on an 2-aryl-1,2,3-propanol represented by the formula (III) in the presence of an acylating agent and allowing to form an optically active 2-aryl-3-acyloxy-1,2-propanediol represented by the formula (VIII).

The concrete examples of enzymes are the same as the above enzymes having stereospecifically hydrolyzing activity or enzymes derived from wheat.

Examples of acylating agent employed in the present invention are carboxylic acids such as acetic acid and butyric acid and carboxylic acid esters such as ethyl acetate, ethyl propionate and vinyl acetate, carboxylic anhydrides such as acetic anhydride, butyric anhydride, fumaric acid, maleic acid and benzoic acid.

The esterification is carried out by the following steps. The substrate is suspended in an organic in a preferable range of 0.1% to 90% (w/v) and then, suitable enzyme, for example at a range of 1:1 to 500:1 (weight ratio of substrate and enzyme) is added to the resulting suspension with stirring at a temperature of 10° to 45° C., preferable 15° to 35° C.

The acylating agent itself can be employed as a solvent and, if necessary, the reaction may be carried out in other organic solvent. Examples of the solvents are toluene, hexane, acetone, diisopropyl ether and dichloromethane. The above solvent can be employed alone or mixed each other. Also, the enzymes can be employed by immobilizing on suitable water-insoluble carried such as ion-exchange resin.

After the esterification, in order to isolate the 2-aryl-3-acyloxy-1,2-propanediol, being product from the reaction liquid, the general isolation method is employed. For example, if necessary, the reaction liquid is filtrated to remove insoluble enzyme and extracted with organic solvent such as ethyl acetate. After the resulting liquid is dried over anhydrous sodium sulfate and the like, the organic solvent is removed under reduced pressure. As the result, the desired optically active 2-aryl-3-acyloxy-1,2-propanediol can be obtained. Furthermore, it can be purified in high purity by purification procedures such as column chromatography on silica gel, crystallization and distillation.

Further, the optically active compound represented by the formula (IX) can be prepared by allowing to react the optically active 2-aryl-3-acyloxy-1,2-propanediol with sulfonic acid halide represented by the formula (X):

 (X)

wherein each X and Y is the same as each of the defined above, in the presence of a base. Examples of bases can be organic bases and inorganic bases such as triethylamine, pyridine and imidazole; and sodium hydroxide and calcium hydroxide. The amount of the employed sulfonic acid halide is preferably about 1.0 to about 1.5 moles to that of the compound (I) being substrate. Also, the mount of the base may be employed about equal to that of the sulfonic acid halide. The reaction is carried out in the organic solvents such as tetrahydrofuran, toluene and ethyl acetate. The temperature of the reaction is a range of −40° to 30° C. After the raction to the resulting liquid is added water and extract with ethyl acetate, remove the solvent and, if necessary, purify by column chromatography on silica gel to give high quality of the optically active compound represented by the formula (XI).

Further, the 2-aryl-2,3-epoxy-1-propanol represented by the formula (XI) can be prepared by adding the compound to a mixed liquid wherein the organic solvent such as toluene is mixed with aqueous solution of strong base such as KOH or NaOH, or in methanol wherein strong base is present, and by taking cyclization and hydrolysis of acylester.

The reaction is completely finished at room temperature for 2 to 24 hours. After the reaction, the desired compound can be obtained by extraction with toluene or ethyl acetate and by removing the solvent. The above compound can be more highly purified by subjecting to column chromatography on silica gel or by distillation. Alternatively, it can be also prepared by allowing to cyclize the organic solvents such as tetrahydrofuran and methylene chloride in the presence of a base and, after isolation of etser, to hydrolize in the presence of a strong base.

An addition of triazole and hydrolysis of acylester are simultaneously carried out by allowing to react the compound represented by the formula (IX) with triazole in the organic solvents such as tetrahydorufan and methanol in the presence of a base such as potassium carbonate or sodium carbonate and 2-aryl-3-(1H-1,2,4-triazole-1-yl)-propane-1, 2-diol can be prepared.

The mount of the base is preferably 2 to 4 equivalents to that of a raw material. The amount of triazole is preferably 2 to 3 equivalents as well as the base.

The reaction is completely finished at a temperature of 40° to 120° C. for 5 to 48 hours. After the reaction, the desired compound can be obtained by removing an inorganic base which is insoluble organic solvent by filtration and by extraction with ethyl acetate then, by removing the solvent. The above compound can be more highly purified by subjecting to column chromatography on silica gel or by recrystallization.

Thus, for example, (R)-2-(2,4-difluorophenyl)-3-(1H-1,2,4-triazole-1-yl)-propane-1,2-diol being useful as an antifungal agent can be prepared.

In order to prepare the 2-aryl-1,2,3-propane triol represented by the formula (III), it is possible to hydrolize 2-aryl-1,3-diacyloxy-2-propanol represented by the formula (I) or 2-aryl-3-acyloxy-1,2-propanediol represented by the formula (VIII) in the presence of a strong base such as KOH or NaOH, or to hydrolize it by enzyme having activity which hydrolyzes it non-stereospecifically. Examples of the above enzymes are Asperigillus genus, lipase obtained from embryo of wheat and cellase obtained from Trichloroderma genus. Examples of those enzymes as a commercially available enzyme are Lipase AP-6 (made by Amano Pharmaceutical Co., Ltd. ) and Lipase (type I) (made by Sigma Chemical Company). The hydrolysis by enzyme can be accomplished using the above enzymes by the same procedure as the process of stereopeficially hydrolysis described above.

For example, by hydrolysis of 2-(2,4-difluorophenyl)-1,3-diacyloxy-2-propanol or 2-(2,4-difluorophenyl)-3-acyloxy-1,2-propanediol in the presence of a strong base such as KOH or NaOH, or by hydrolysis it by enzyme having activity which hydrolysis it non-stereospecifically, 2-(2,4-difluorophenyl)-1,2,3-propanetriol can be prepared.

Those 2-aryl-1,2,3-propanetriol can be isolated as a highly purified compound by extraction with ethyl acetate from reaction liquid and by removing the solvent and then by purification by column chromatography on silica gel.

BEST MODE FOR CARRYING OUT THE INVENTION

Hereinafter, the present invention is more specifically explained on the basis of the following Examples, but is not limited to only these Examples.

EXAMPLE 1

Synthesis of 1,3-diacetoxy-2-(2 4-difluorophenyl)-2-propanol (according to Reaction formula 1)

Under an atmosphere of argon, 850 ml of THF solution of 2,4-difluorophenylmagnesium bromide prepared from 202.6 g (1.05 mol) of 2,4-difluorobromobenzene and 26.7 g (1.1 mol) of magnesium turnings was added dropwise at –30° C. to 1.7 l of THF solution of 174 g (1.00 mol) of 1,3-diacetoxyacetone which was previously cooled to –30° C. After the resulting liquid was stirred at –60° C. for 2 hours, a temperature thereof was gradually raised to room temperature. Then, to the reaction mixture was added 1 l of 1.2N aqueous solution of hydrochloric acid at 5° C. or below, and an aqueous layer was extracted twice with 1 l of ethyl acetate. The organic layer was washed with saturated aqueous solution of sodium chloride, dried and concentrated under reduced pressure to give 302 g of crude oil. The obtained oil was purified by means of column chromatography on silica gel (hexane: ethyl acetate=1:1) to give 125 g of the desired compound. The compound was recrystallized from toluene/hexane.

m.p.: 70.5°–71.5° C. IR ν cm$^{-1}$: 3403, 1744, 1240, 1042, 849 $^1$H-NMR (400 MHz, CDCl$_3$) δ ppm:7.70–7.67 (m; 1H), 6.93(t; J=5.37 Hz, 1H), 6.81 (t; J=2.93 Hz, 1H), 4.52 (d; J=11.72 Hz, 2H), 4.44 (d; J=11.72 Hz, 2H), 3.65(s; 1H), 2.03 (s; 6H)

EXAMPLE 2

Synthesis of 1,3-diacetoxy-2-(2,4-difluorophenyl)-2-propanol (according to Reaction formula 1)

The reaction was carried out in the same manner as described in Example 1 except that diethyl ether was employed instead of THF as a solvent. From 202.6 g of 2,4-difluorobromobenzene was prepared 100 g of the desired compound.

EXAMPLE 3

Synthesis of 1,3-diacetoxy-2-(2,4-difluorophenyl)-2-propanol (according to Reaction formula 1), Under an atmosphere of argon, 22.5 g of 2,4-difluorobromobenzene was dissolved in 200 ml of diethyl ether and to the resulting solution was added dropwise 73 ml of 1.63M n-hexane solution of n-butyllithium at –30° C. The resulting liquid was stirred for 1 hour and stored at –60° C. This liquid was carefully added dropwise using an injection cylinge to 150 ml of diethyl ether solution of 17.4 g of 1,3-diacetoxyacetone which was previously cooled to –30° C. After the resulting liquid was stirred at –60° C. for 2 hours, a temperature thereof was gradually raised to room temperature. Then, the reaction mixture was transferred to 100 ml of 1.2N aqueous solution of hydrochloric acid at 5° C. or below, and the organic layer was separated therefrom and the aqueous layer was extracted twice with 100 ml of ethyl acetate. The organic layers were combined and washed with saturated aqueous solution with sodium chloride, dried over anhydrous magnesium sulfate. The resulting organic layer was filtered and the solvent was removed under reduced pressure. Thus obtained concentrate was purified by column chromatography on silica gel (hexane: ethyl acetate=1:1) to give 8 g of the desired compound.

EXAMPLE 4

Synthesis of 1, 3-diacetoxy-2-(2,4-difluorophenyl)-2-propanol (according to Reaction formula 2)

In 100 ml of pyridine was dissolved 10 g of 2-(2,4-difluorophenyl)-1,2,3-propanetriol. To the resulting solution was added dropwise 1.1 g of acetic anhydride at room temperature. After the dropping, the resulting liquid was stirred at room temperature for 1 hour. Then, to the reaction mixture was added 50 ml of ethyl acetate, and an organic layer was separated therefrom. After the organic layer was washed with 1N aqueous solution of hydrochloric acid and further washed with water and saturated aqueous solution with sodium chloride. Then the organic layer was dried over anhydrous sodium sulfate. The resulting organic layer was filtered and the solvent was removed under reduced pressure. Thus obtained concentrate was purified by column chromatography on silica gel (hexane: ethyl acetate=1:1) to give 12.5 g of the desired compound.

EXAMPLE 5

Synthesis of 1-chloro-2-(2,4-difluorophenyl)-2,3-epoxypropane (according to Reaction formula 3)

To 1.7 l of toluene solution of 433 g of 1,3-dichloro-2-(2,4-difluorophenyl)-2-propanol was added 870 ml of 20% aqueous solution of potassium hydroxide. After the resulting liquid was stirred at room temperature for 3 hours, the organic layer was separated therefrom. The aqueous layer was extracted twice with 1 l of ethyl acetate. The organic layers were combined and dried over anhydrous sodium sulfate. The resulting organic layer was filtered and the solvent was removed under reduced pressure. Thus obtained concentrate was distilled under reduced pressure to give 184 g of the desired compound.

b.p. : 125°–135° C./30 mmHg $^1$H-NMR (90 MHz, CDCl$_3$) δ ppm: 7.57–7.31 (1H, m), 6.98–6.71 (2H, m), 4.09 (1H, d, J=11.9 Hz), 3.68 (1H, d, J=11.9 Hz), 3.20 (1H, d, J=4.8 Hz), 2.93(1H, d, J=4.8 Hz) IR ν cm$^{-1}$: 1619, 1602, 1508, 1425, 1272

EXAMPLE 6

Synthesis of 1,3-diacetoxy-2-(2,4-difluorophenyl)-2-propanol (according to Reaction formula 3)

To 105 g of 1-chloro-2-(2, 4-difluorophenyl)-2,3-epoxypropane were added 525 ml of acetic acid and 126 g of potassium acetate and the resulting mixture was stirred at 115° C. for 15 hours. The reaction mixture was allowed to cool to room temperature. Then, to this reaction liquid was added 700 ml of water and a solid matter was dissolved and the resulting solution was extracted three times with 500 ml of ethyl acetate. The organic layer was washed with saturated aqueous solution with sodium hydrogencarbonate and with water and dried over anhydrous sodium sulfate. The resulting organic layer was filtered and the solvent was removed under reduced pressure. Thus obtained concentrate was purified by column chromatography on silica gel (hexane: ethyl acetate=1:1) to give 100 g of the desired compound.

EXAMPLE 7

Synthesis of 1,3-diacetoxyacetone

Under an atmosphere of argon, 90 g of 1,3-dihydroxyacetone dimer and 250 mg of 4-(N,N-dimethylamino)pyridine were dissolved in 250 ml of pyridine. To the resulting solution, 225 ml of acetic anhydride was added dropwise at room temperature over 1 hour. After the resulting liquid was stirred at room temperature for 30 minutes, thereto was added 50 ml of methanol and the resulting liquid was further stirred at room temperature for 30 minutes. The solvent was removed under reduced pressure and the residue was subjected to a recrystallization from ether-petroleum ether to give 190 g of the desired compound.

m.p.: 45.5°–46.6° C. $^1$H-NMR (400 MHz, CDCl$_3$) δ ppm: 2.18(s, 6H), 4.76 (s, 4H) IR ν cm$^{-1}$: 1770, 1745, 1230

EXAMPLE 8

Synthesis of 1,3-di-n-butylyloxyacetone

Under an atmosphere of argon, 45 g of 1,3-dihydroxyacetone dimer and 100 mg of 4-(N,N-dimethylamino)pyridine were dissolved in 120 ml of pyridine. To the resulting solution, 196 ml of n-butyric anhydride was added dropwise at room temperature over 1 hour. After the resulting mixture was stirred at room temperature for 30 minutes, thereto was added 50 ml of methanol and the resulting mixture was further stirred at room temperature for 30 minutes. To the reaction mixture was added 1 l of ethyl acetate and the organic layer was separated. The organic layer was washed with 2N HCl and further washed with saturated aqueous solution with sodium hydrogencarbonate and saturated aqueous solution with sodium chloride, and dried over anhydrous sodium sulfate. The solvent was removed under reduced pressure. The residue was subjected to a recrystallization from ether/n-hexane to give 98.6 g of the desired compound.

m.p.: 47°–48° C. $^1$H-NMR (400 MHz, CDCl$_3$) δ ppm: 4.76 (s, 4H), 2.42 (t, 4H, J=7.3 Hz), 1.65–1.75 (m, 4H), 0.99 (t, 6H, J=7.3 Hz) IR ν cm$^{-1}$: 1736, 1418, 1179, 1094, 994

EXAMPLE 9

Synthesis of 1,3-dipropionyloxyacetone

Under an atmosphere of argon, 45 g of 1,3-dihydroxyacetone dimer and 100 mg of 4-(N,N-dimethylamino)pyridine were dissolved in 120 ml of pyridine. To the resulting solution, 150 ml of propionic anhydride was added dropwise at room temperature over 1 hour. After the resulting liquid was stirred at room temperature for 30 minutes, thereto was added 50 ml of methanol and the resulting liquid was further stirred at room temperature for 30 minutes. To the reaction mixture was added 1 l of ethyl acetate and the organic layer was separated. The organic layer was washed with 2N HCl and further washed with saturated aqueous solution with sodium hydrogencarbonate and saturated aqueous solution with sodium chloride, and dried over anhydrous sodium sulfate. The solvent was removed under reduced pressure. The residue was subjected to a recrystallization from ether/n-hexane to give 74 g of the desired compound.

$^1$H-NMR (400 MHz, CDCl$_3$) δ ppm: 4.77(s, 4H), 2.47 (q, 4H, J=7.3 Hz), 1.19 (t, 6H, J=7.3 Hz)

EXAMPLE 10

Synthesis of 1,3-diisobutyryloxyacetone

A 100 ml reaction vessel was charged with 4.18 g of dihydroxyacetone (monomer), 11.2 ml of pyridine and 10 mg of 4-dimethylaminopyridine and the mixture was stirred at room temperature. Thereto was added dropwise 16.7 ml of isobutyric anhydride over 30 minutes. After the dropping, the resulting liquid was further stirred for 1 hour and then 1 ml of methanol was added thereto and the resulting liquid was further stirred for 1 hour. To the reaction mixture was added ethyl acetate and the organic layer was separated. The organic layer was washed with water and further washed with saturated aqueous solution with sodium bicarbonate and 1N HCl. Then, the solvent was removed under reduced pressure. The residue was distilled under reduced pressure to give 7.47 g of the desired compound.

b.p. 91°–103° C./0.5 mmHg $^1$H-NMR(400 MHz, CDCl$_3$) δ ppm: 4.76(4H, s), 2.72–2.65(2H, m), 1.24–1.22(12H, d)

EXAMPLE 11

Synthesis of 1,3-dipropionyloxy-2-(2,4-difluorophenyl)-2-propanol (according to Reaction formula 2)

In 30 ml of pyridine was dissolved 3.06 g of 2-(2,4-difluorophenyl)-1,2,3-propanetriol and thereto was added dropwise 4.29 g of propionic anhydride and stirred at room temperature for 6 hours. To thus obtained reaction liquid was added 100 ml of ethyl acetate and the organic layer was separated. The organic layer was washed with 1N HCl and further washed with water and saturated aqueous solution with sodium chloride. After the organic layer was dried over anhydrous sodium sulfate, the solvent was removed under reduced pressure. Thus obtained concentrate was purified by means of column chromatography on silica gel (hexane/ethyl acetate=2/1) to give 4.55 g of the oily desired compound.

$^1$H-NMR (400 MHz, CDCl$_3$) δ ppm: 7.71–7.67 (1H, m), 6.94–6.89 (1H, m), 6.83–6.78 (1H, m), 4.54–4.43 (4H, dd), 3.77 (1H, s), 2.32–2.26(2H, q), 1.08–1.04(3H, t)

EXAMPLE 12

Synthesis of 1,3-di-n-pentanoyl-2-(2,4-difluorophenyl)-2-propanol (according to Reaction formula 2)

In 30 ml of pyridine was dissolved 3.06 g of 2-(2,4-difluorophenyl-1,2,3-propanetriol and thereto was added dropwise 9.05 g of valeryl chloride and stirred at room temperature for 6 hours. To the reaction mixture was added 30 ml of water and the resulting liquid was extracted with 100 ml of ethyl acetate. The organic layer was washed with saturated aqueous solution with sodium bicarbonate and further washed with water and with saturated aqueous solution with sodium chloride. The organic layer was dried over anhydrous sodium sulfate and the solvent was removed under reduced pressure. Thus obtained concentrate was purified by column chromatography on silica gel (hexane/ethyl acetate=2/1) to give 3.16 g of the oily desired compound.

$^1$H-NMR (400 MHz, CDCl$_3$) δ ppm: 7.72–7.64 (1H, m), 6.95–6.88 (1H, t), 6.85–6.78 (1H, m), 4.52–4.44 (4H, dd), 2.40–2.35 (2H, m), 2.30–2.25 (2H, m), 1.66–1.58 (2H, m), 1.55–1.45 (2H, m), 1.43–1.33 (2H, m), 1.30–1.18 (2H, m), 0.96–0.90 (3H, m), 0.88–0.82 (3H, m)

EXAMPLE 13

Synthesis of 1,3-di-n-butyryloxy-2-(2,4-difluorophenyl)-2-propanol (according to Reaction formula 2)

In 30 ml of pyridine was dissolved 3.06 g of 2-(2,4-difluorophenyl)-1,2,3-propanetriol and thereto was added dropwise 5.22 g of n-butyric anhydride and stirred at room temperature for 6 hours. To thus obtained reaction liquid was added 100 ml of ethyl acetate and the organic layer was separated. The organic layer was washed with 1N HCl, further washed with water and saturated aqueous solution with sodium chloride. After the organic layer was dried over anhydrous sodium sulfate, the solvent was removed trader reduced pressure. Thus obtained concentrate was purified by column chromatography on silica gel (hexane/ethyl acetate=2/1) to give 5.12 g of the oily desired compound.

$^1$H-NMR (400 MHz, CDCl$_3$) δ ppm: 7.72–7.65 (1H, m), 6.95–6.88 (1H, t), 6.85–6.76 (1H, m), 4.55–4.44 (4H, dd), 3.82 (1H, s), 2.28–2.23 (4H, m), 1.60–1.50 (4H, m), 0.88–0.83 (6H, t)

EXAMPLE 14

Synthesis of 1,3-diisobutyryloxy-2-(2,4-difluorophenyl-2-propanol (according to Reaction formula 1)

Under an atmosphere of argon, 5 ml of THF was slowly added to 925 mg of magnesium turnings, and then thereto was added dropwise 7 g of 2,4-difluorobromobenzene dissolved in 30 ml of THF with keeping the temperature at 20° C. After the reaction mixture was stirred for 1 hour with keeping the temperature at 20° C., 7.9 g of 1,3-diisobutyryloxyacetone dissolved in 10 ml of THF was added dropwise thereto with keeping the temperature at 0° C. After the dropping, the reaction mixture was stirred for 4 hours and then the reaction was stopped by adding 35 ml of 1N sulfuric acid. The obtained liquid was extracted twice with 35 ml of ethyl acetate. The organic layer was washed with saturated aqueous solution with sodium bicarbonate and with saturated aqueous solution with sodium chloride, in turn. The solvent was removed under reduced pressure. Thus obtained concentrate was distilled under reduced pressure to give 10 g of the desired compound.

b.p. 114°–119° C./0.5–0.6 mmHg $^1$H NMR(400 MHz, CDCl$_3$) δ ppm: 7.73–7.65 (1H, m), 6.95–6.88 (1H, t), 6.85–6.77 (1H, m), 4.54–4.45 (4H, q), 3.90 (1H, s), 2.55–2.47 (2H, m), 1.10–1.03 (12H, m)

EXAMPLE 15

Synthesis of 1,3-diisobutyryloxy-2-phenyl-2-propanol (according to Reaction formula 1)

Under an atmosphere of argon, 2 ml of diethyl ether was slowly added to 695 mg of magnesium turnings, and then thereto was added dropwise 4 g of bromobenzene dissolved in 10 ml of diethyl ether. The resulting liquid was stirred for 1 hour under refluxing and allowed to cool. That liquid was added dropwise to 50 ml of diethyl ether solution of 3.78 g of 1,3-diisobutyryloxyacetone which was previously cooled to –50° C. After the resulting liquid was stirred at –50° C. for 1 hour, a temperature thereof was gradually raised to room temperature. Then, the reaction mixture was added to 50 ml of 2N aqueous solution of hydrochloric acid at 5° C. or below, and an organic layer was separated and the aqueous layer was extracted twice with 50 ml of ethyl acetate. The organic layers were combined and washed three times with 1N aqueous solution of sodium hydroxide, washed twice with saturated aqueous solution with sodium chloride, and dried over anhydrous sodium sulfate. The solvent was removed under reduced pressure. The residue was purified by column chromatography on silica gel (eluent: n-hexane/ethyl acetate=1/1) to give 5.5 g of the desired compound.

$^1$H-NMR (400 MHz, CDCl$_3$) δ ppm: 7.48–7.46 (2H, m), 7.39–7.37 (2H, m), 7.35–7.28 (1H, m), 4.43–4.35 (4H, q), 3.15 (1H, s), 2.56–2.49 (2H, m), 1.11–1.07 (12H, t)

EXAMPLES 16 TO 27

An diester shown in Table 3 was obtained by carrying out the same manner as described in Example 15 employing a compound shown in Table 3 instead of bromobenzene as a starting substance. A $^1$H-NMR spectra of that ester was shown in Table 4.

TABLE 3

| Example No. | Raw Material | Diester |
|---|---|---|
| 16 | 4-Fluorobromobenzene | 2-(4-Fluorophenyl)-1,3-diisobutyryloxy-2-propanol |
| 17 | 4-Chlorobromobenzene | 2-(4-Chlorophenyl)-1,3-diisobutyryloxy-2-propanol |
| 18 | 4-Bromotoluene | 2-(4-Methylphenyl)-1,3-diisobutyryloxy-2-propanol |
| 19 | 4-Bromobiphenyl | 2-(4-Biphenyl)-1,3-diisobutyryloxy-2-propanol |
| 20 | 4-Bromoanisole | 2-(4-Methoxyphenyl)-1,3-diisobutyryloxy-2-propanol |
| 21 | 1-Bromo-4-t-butylbezene | 2-(4-t-Butylphenyl)-1,3-diisobutyryloxy-2-propanol |
| 22 | 2-Chlorobromobenzene | 2-(2-Chlorophenyl)-1,3-diisobutyryloxy-2-propanol |
| 23 | 2-Bromotoluene | 2-(4-Methylphenyl)-1,3-diisobutyryloxy-2-propanol |
| 24 | 2,4-Dichloroiodobenzene | 2-(2,4-Dichlorophenyl)-1,3-diisobutyryloxy-2-propanol |
| 25 | 4-Bromo-m-xylene | 2-(2,4-Dimethylphenyl)-1,3-diisobutyryloxy-2-propanol |
| 26 | 1-Bromonaphthalene | 2-(1-Naphthyl)-1,3-diisobutyryloxy-2-propanol |
| 27 | 2-Bromonaphthalene | 2-(2-Naphthyl)-1,3-diisobutyryloxy-2-propanol |

TABLE 4

| Ex. No. | $^1$H-NMR (400 MHz, CDCl$_3$) δ ppm |
|---|---|
| 16 | 7.49–7.45(2H, m), 7.07–7.03(2H, m), 4.40–4.32 (4H, q), 3.27(1H, s), 2.57–2.50(2H, m), 1.27–1,21 (12H, m) |
| 17 | 7.44–7.33(4H, dd), 4.39–4.32(4H, q), 3.23(1H, s), 2.56–2.50(2H, m), 1.11–1.08(12H, m) |
| 18 | 7.37–7.16(4H, dd), 4.40–4.33(4H, q), 3.12(1H, s), 2.57–2.50(2H, m), 2.04(3H, s), 1.12–1.08(12H, m) |
| 19 | 7.61–7.54(6H, m), 7.45–7.42(2H, m), 7.37–7.35 (1H, m), 4.47–4.38(4H, q), 3.26(1H, s), 2.56–2.51 (2H, m), 1.12–1.09(12H, m) |
| 20 | 7.41–6.88(4H, dd), 4.40–4.32(4H, q), 3.81(3H, s), 3.02(1H, s), 2.57–2.50(2H, m), 1.12–1.09(12H, m) |
| 21 | 7.41–7.36(4H, m), 4.43–4.33(4H, m), 3.02(1H, s), 2.57–2.50(2H, m), 1.31(9H, s), 1.11–1.07(12H, m) |
| 22 | 7.85–7.82(1H, d), 7.37–7.35(1H, d), 7.32–7.24 (2H, m), 4.75–4.68(4H, q), 4.20(1H, s), 2.52–2.45 (2H, m), 1.23(2H, d), 1.04–1.01(10H, m) |
| 23 | 7.44–7.42(1H, d), 7.21–7.15(3H, m), 4.55–4.48 (4H, q), 3.34(1H, s), 2.57(3H, s), 2.55–2.48(2H, m), 1.26–1.22(2H, d), 1.07–1.06(10H, m) |
| 24 | 7.81–7.79(1H, d), 7.39(1H, d), 7.29–7.27(1H, m), 4.68(4H, s), 4.21(1H, s), 2.53–2.46(2H, m), 1.06–1.03(12H, m) |
| 25 | 7.29–7.26(1H, d), 6.98–6.95(2H, d), 4.52–4.45 (4H, q), 3.23(1H, s), 2.55–2.49(2H, m), 2.53(3H, s), 2.28(3H, s), 1.10–1.07(12H, m) |
| 26 | 8.71(1H, m), 7.88–7.81(1H, m), 7.58–7.40(5H, m), 4.81–4.67(4H, m), 3.43(1H, s), 2.55–2.48(2H, m), 1.21–1.16(2H, m), 1.08–1.05(10H, m) |
| 27 | 7.98(1H, d), 7.86–7.81(3H, m), 7.58–7.56(1H, d), 7.51–7.47(2H, m), 4.52–4.45(4H, q), 3.32(1H, s), 2.55–2.48(2H, m), 1.23–1.21(2H, m), 1.09–1.06 (10H, m) |

EXAMPLE 28

Synthesis of 2-(2,4-difluorophenyl)-3-acetoxy-1,2-propanediol

Each test tube was charged with 10 mg of 2-(2,4-difluorophenyl)-1,3-diacetoxy-2-propanol, each 10 mg of the enzymes shown in Table 1 (Enzyme Nos. 1 to 10), 1 ml of 50 mM acetate buffer (pH 5) and 1 ml of n-hexane. The each test tube was shaken at 30° C. for 16 hours. Then, thereto was added 1 ml of ethyl acetate and the resulting liquid was extracted. The solvent was removed under reduced pressure to give an oily residue. The oily residue was dissolved in methanol and HPLC analysis was carried out to estimate a conversion ratio into the formed 2-(2,4-difluorophenyl)-3-acetoxy-1,2-propanediol and an optical purity thereof, and the results were shown in Table 5 (Conditions for carrying out the HPLC analysis/column: CHIRALPAK AD (0.46×25 cm), made by Daicel Chemical Industries, Ltd., eluent: n-hexane/ethanol=9/1, detection wavelength: 254 nm, flow rate: 1 ml/min, temperature of the column: room temperature).

TABLE 5

| Enzyme No. | Conversion Ratio (%) | Optical Purity (% ee) |
|---|---|---|
| 1 | 34.3 | (R) (−) 70.0 |
| 2 | 59.8 | (R) (−) 75.0 |
| 3 | 96.2 | (R) (−) 93.2 |
| 4 | 39.8 | (R) (−) 90.7 |
| 5 | 55.8 | (R) (−) 85.7 |
| 6 | 85.4 | (R) (−) 91.8 |
| 7 | 44.0 | (R) (−) 89.8 |
| 8 | 40.2 | (R) (−) 71.3 |
| 9 | 42.8 | (S) (+) 86.9 |

EXAMPLE 29

Synthesis of (R)-2-(2,4-difluorophenyl)-3-acetoxy-1,2-propanediol

A 10 l reaction vessel was charged with 110 g of 2-(2,4-difluorophenyl)-1,3-diacetoxy-2-propanol, 11 g of Lipase made by SEIKAGAKU CORPORATION, (derived from *Rhizopus delemar*, Enzyme No. 3), 2.8 l of 50 mM acetate buffer (pH 5) and 2.8 l of cyclohexane. The resulting mixture was stirred at 30° C. for 47 hours. The obtained reaction mixture was extracted twice with 3 l of ethyl acetate and the organic layers were combined and dried over anhydrous sodium sulfate. The solvent was removed under reduced pressure to give 90 g of (R)-2-(2,4-difluorophenyl)-3-acetoxy-1,2-propanediol.

$^1$H-NMR (400 MHz, CDCl$_3$) δ ppm: 7.69–7.65 (1H, m), 6.92 (1H, t, J=5.37 Hz), 6.80 (1H, t, J=2.93 Hz), 4.52 (2H, s), 3.97 (1H, d, J=3.42 Hz), 3.80 (1H, d, J=3.42 Hz), 3.91 (1H, s), 2.00 (3H, s) IR; ν cm$^{-1}$: 3420, 1711, 1501, 1240, 1055, 970, 847 $[\alpha]_D^{25}$=−4.72° (c=1.02, CH$_3$OH) Optical purity: 98.2% ee m.p.: 52°–53° C.

EXAMPLE 30

Synthesis of (S)-2-(2,4-difluorophenyl)-1-acetoxy-3-methanesulfonyloxy-2-propanol To a solution wherein 104 g of (R)-2-(2,4-difluorophenyl)-3-acetoxy-1,2-propanediol was dissolved in 1000 ml of tetrahydrofuran was added 55.7 g of triethylamine at a temperature of −10° to 0° C., and thereto was added dropwise 117 g of methanesulfonyl acid chloride dissolved in 400 ml of tetrahydrofuran over 30 minutes. After the resulting liquid was stirred at the same temperature for 1 hour, the reaction mixture was poured into 500 ml of water and extracted with ethyl acetate. The ethyl acetate-layer was dried over anhydrous sodium sulfate and the solvent was removed. The obtained residue was purified by column chromatography on silica gel (eluent: n-hexane/ethyl acetate=1/1) to give 130 g of (S)-2-(2,4-difluorophenyl)-1-acetoxy-3-methane-sulfonyloxy-2-propanol.

$^1$H-NMR (400 MHz, CDCl$_3$) δ ppm: 7.73–7.67 (1H, m), 6.85 (1H, t, J=2.44 Hz), 6.82 (1H, t, J=6.35 Hz), 4.63–4.55 (4H, m), 3.05 (1H, s), 3.03 (3H, s), 2.04 (3H, s) IR; ν cm$^{-1}$: 3500, 1740, 1500, 1355, 1175, 970, 845 [α]$_D^{25}$=−11.7° (c=1.01, CH$_3$OH)

EXAMPLE 31

Synthesis of (S)-2-(2,4-difluorophenyl)-2,3-epoxy-1-propanol

In 250 ml of toluene was dissolved 50 g of (S)-2-(2,4-difluorophenyl)-1-acetoxy-3-methanesulfonyloxy-2-propanol and thereto was added 250 ml of 20% aqueous solution of potassium hydroxide and then the resulting liquid was stirred at room temperature for 12 hours. A toluene-layer was separated and the aqueous layer was extracted three times with 100 mg of ethyl acetate. The organic layers were combined and dried over anhydrous sodium sulfate and the solvent was removed. The residue was purified by column chromatography on silica gel to give 21 g of (S)-2-(2,4-difluorophenyl)-2,3-epoxy-1-propanol. The optical purity thereof was determined by HPLC analysis (column: CHIRALPAK AS made by Daicel Chemical Industries, Ltd., eluent: n-hexane/isopropanol=98/2, detection wavelength: 254 nm, flow rate: 1.2 ml/min).

$^1$H-NMR (400 MHz, CDCl$_3$) δ ppm: 7.43–7.37 (1H, m), 6.91–6.79 (2H, m), 4.04–4.00 (1H, m), 3.93–3.88 (1H, m), 3.30 (1H, d, J=4.89 Hz), 2.84 (1H, d, J=5.37 Hz), 1.89–1.85 (1H, m) IR; ν cm$^{-1}$: 3450, 1620, 1510, 1270, 1040, 965, 850 [α]$_D^{25}$=−39.2° (c=1.02, CH$_3$OH) Optical purity: 95.2% ee

EXAMPLE 32

Synthesis of 2-(2,4-difluorophenyl)-1,2,3-propanetriol

A 2 l reaction vessel was charged with 10 g of 2-(2,4-difluorophenyl)-1,3-diacetoxy-2-propanol, 2 g of Lipase AP-6 (made by Amano Pharmaceutical Co., Ltd., derived from *Aspergillus niger*, Enzyme No. 12), 500 ml of 50 mM phosphate buffer (pH 7.0) and 500 ml of cyclohexane. The resulting mixture was stirred at 30° C. for 24 hours. The reaction liquid was extracted three times with 1000 ml of ethyl acetate and dried over anhydrous sodium sulfate. The solvent was removed under reduced pressure and the residue was purified by column chromatography on silica gel (n-hexane/ethyl acetate=1/10) to give 6.6 g of 2-(2,4-difluorophenyl)-1,2,3-propanetriol.

$^1$H-NMR(400 MHz, CDCl$_3$) δ ppm:7.73–7.68 (1H, m), 6.92(1H, t, J=8.11 Hz), 6.79(1H, t, J=2.93 Hz), 4.13(2H, d, J=12.21 Hz), 3.80(3H, t, J=11.23 Hz) IR; ν cm$^{-1}$: 3382, 1622, 1503, 1123, 1071, 994, 968, 851 m.p.: 58°–59° C.

EXAMPLE 33

Synthesis of 2-(2,4-difluorophenyl)-1,2,3-propanetriol

In a 200 ml reaction vessel, 10 g of 2-(2,4-difluorophenyl)-1,3-diacetoxy-2-propanol was dissolved in 30 ml of toluene and thereto was added 30 ml of 30% aqueous KOH solution. The resulting liquid was stirred at room temperature for 24 hours and more. Then a toluene-layer and an aqueous layer were separated from each other and the aqueous layer was extracted twice with 50 ml of ethyl acetate. The organic layer was washed with brine and then dried over anhydrous sodium sulfate. The solvent was removed therefrom and the residue was purified in the same manner as in Example 32 to give 6.5 g of 2-(2,4-difluorophenyl)-1,2,3-propanetriol.

EXAMPLE 34

Synthesis of (S)-2-(2,4-difluorophenyl)-1-acetoxy-1,2-propanediol

A 300 ml reaction vessel was charged with 5 g of 2-(2,4-difluorophenyl)-1,2,3-propanetriol, 100 ml of diisopropanol, 2.45 ml of acetic anhydride and 5 g of Novozym 435 made by NOVO NORDISK, Ltd. (derived from *Candida antarctica*, Enzyme No. 24). The resulting mixture was stirred at 30° C. for 15 hours. After 10 ml of water was added thereto, the reaction liquid was filtered to remove the enzyme. An organic layer of the filtrate was dried over anhydrous sodium sulfate and the solvent was removed under reduced pressure. The residue was purified by column chromatography on silica gel (n-hexane/ethyl acetate=1/1) to give 1 g of (S)-2-(2,4-difluorophenyl)-1-acetoxy-1,2-propanediol. The optical purity thereof was 8% ee.

EXAMPLE 35

Each test tube was charged with 100 mg of 2-(2,4-difluorophenyl)-1,3-diisobutyryloxy-2-propanol, 10 mg of Lipase D (Enzyme No. 6), 0.9 ml of 50 mM acetate buffer (pH 5) and each 0.1 ml of the organic solvents shown in Table 6. The test tube was shaken at 30° C. for 16 hours. Then, thereto was added 5 ml of ethyl acetate and the resulting liquid was extracted. The solvent was removed under reduced pressure to give an oily residue. The oily residue was dissolved in methanol and HPLC analysis was carried out. Each ratio of the formed (R)-2-(2,4-difluorophenyl)-3-isobutyryloxy-1,2-propanediol (mono ester), 2-(2,4-difluorophenyl)-1,2,3-propanetriol (triol) and the residual substrate (diester) and an optical purity of the formed monoester were shown in Table 6. (The conditions for carrying out the HPLC analysis/column: CHIRALPAK AD (0.46 mm×25 cm) made by Daicel Chemical Industries, Ltd., eluent: n-hexane/ethanol=9/1, detection wavelength: 254 nm, flow rate: 1.2 ml/min, temperature of the column: room temperature, elution time: 7.8 minutes (the diester), 12.3 minutes ((S) monoester), 17.4 minutes ((R) monoester) and 22.0 minutes (triol)).

TABLE 6

| Added Organic Solvent | Diester (%) | Monoester (%) | Monoester (% ee) | Triol (%) |
|---|---|---|---|---|
| Diisopropyl ether | 50.07 | 48.83 | 90.89 | 1.10 |
| n-Hexane | 51.34 | 47.36 | 92.95 | 1.30 |
| Cyclohexane | 37.09 | 61.26 | 96.29 | 1.65 |
| n-Heptane | 45.27 | 53.09 | 94.77 | 1.64 |
| n-Octane | 42.17 | 56.43 | 87.89 | 1.41 |
| n-Decane | 45.17 | 53.36 | 91.15 | 1.47 |
| Petroleum ether | 46.44 | 52.47 | 90.57 | 1.09 |
| Benzene | 43.84 | 54.84 | 92.13 | 1.33 |
| Toluene | 49.10 | 49.58 | 91.21 | 1.33 |
| Chloroform | 48.02 | 50.19 | 92.09 | 1.78 |
| Methylcyclohexane | 45.06 | 53.86 | 94.90 | 1.08 |
| Isooctane | 47.87 | 51.09 | 94.64 | 1.04 |
| None | 52.46 | 46.57 | 89.13 | 0.97 |

EXAMPLE 36

Each test tube was charged with 20 mg of 2-(2,4-difluorophenyl)-1,3-diisobutyryloxy-2-propanol, each 2 mg of the enzymes shown in Tables 1 and 2 and 1 ml of 50 mM acetate buffer (pH 5). The test tube was shaken at 30° C. for 16 hours. Then, thereto was added 5 ml of ethyl acetate and the resulting liquid was extracted. The solvent was removed under reduced pressure to give an oily residue. The oily residue was dissolved in methanol and HPLC analysis was carried out in the same manner as in Example 35. Each ratio of the formed 2-(2,4-difluorophenyl)-3-isobutyryloxy-1,2-propanediol (monoester), 2-(2,4-difluorophenyl)-1,2,3-propanetriol (triol) and the residual substrate (diester) and an optical purity of the formed monoester were shown in Table 7.

TABLE 7

| Enzyme No. | Diester (%) | Monoester (%) | Monoester (% ee) | Triol (%) |
|---|---|---|---|---|
| 11 | 72.61 | 22.58 | (R) 44.24 | 4.81 |
| 12 | 63.75 | 27.75 | (R) 45.73 | 8.50 |
| 13 | 42.06 | 57.72 | (R) 96.78 | 0.21 |
| 14 | 0.04 | 8.04 | (R) 67.45 | 91.93 |
| 2 | 1.03 | 94.47 | (R) 97.41 | 4.50 |
| 4 | 65.66 | 34.17 | (R) 97.49 | 0.17 |
| 5 | 35.90 | 63.65 | (R) 97.80 | 0.45 |
| 6 | 26.15 | 72.97 | (R) 97.53 | 0.88 |
| 15 | 20.80 | 78.35 | (R) 97.42 | 0.85 |
| 16 | 85.41 | 14.39 | (R) 95.66 | 0.20 |
| 17 | 99.87 | 0.31 | (S) 23.16 | 0 |
| 18 | 71.38 | 28.56 | (R) 97.65 | 0.06 |
| 19 | 35.89 | 58.45 | (R) 87.75 | 5.66 |
| 20 | 2.64 | 5.21 | (R) 76.56 | 92.15 |
| 21 | 0 | 14.27 | (R) 95.37 | 85.73 |
| 22 | 81.79 | 17.13 | (S) 48.29 | 1.08 |
| 10 | 0.59 | 14.66 | (R) 10.55 | 84.75 |
| 23 | 89.56 | 9.65 | (S) 72.29 | 0.79 |
| 24 | 94.51 | 5.00 | (S) 12.45 | 0.48 |
| 25 | 98.17 | 1.83 | (R) 44.11 | 0 |
| 26 | 90.73 | 8.65 | (S) 72.42 | 0.62 |

EXAMPLE 37

Synthesis of (R)-2-(2,4-difluorophenyl)-3-propionyloxy-1,2-propanediol

A 200 ml reaction vessel was charged with 3 g of 2-(2,4-difluorophenyl)-1,3-dipropionyloxy-2-propanol, 200 mg of Lipase D made by Amano Pharmaceutical Co., Ltd. (derived from *Rhizpus delemer*, Enzyme No. 6), 100 ml of 50 mM acetate buffer (pH 5) and 10 ml of cyclohexane. The resulting mixture was stirred at 30° C. to react for 18 hours. After the reaction liquid was extracted three times with 50 ml of ethylacetate, the organic layers were combined and the combined organic layer was washed with saturated aqueous solution with sodium bicarbonate and with saturated aqueous solution with sodium chloride and dried over anhydrous sodium sulfate. The solvent was removed trader reduced pressure and the residue was purified by column chromatography on silica gel (eluent: n-hexane/ethyl acetate=1/1) to give 1.55 g of oily (R)-2-(2,4-difluorophenyl)-3-propionyloxy-1,2-propanediol. An optical purity thereof was determined in the same manner as in Example 35. (Elution time: 16.7 minutes ((R)-form) and 13.5 minutes ((S)-form)).

$^1$H-NMR (400 MHz, CDCl$_3$) δ ppm: 7.69–7.63 (1H, m), 6.98–6.89 (1H, m), 6.88–6.77 (1H, m), 4.57–4.50 (2H, q), 3.99–3.96 (2H, d), 3.80–3.77 (1H, d), 2.38 (1H, s), 2.29–2.22 (2H, m), 1.04–1.00 (3H, t) $[α]_D^{25}$=–4.40° (C=1.011, CH$_3$OH) Optical purity: 84.6% ee

EXAMPLE 38

Synthesis of (R)-2-(2,4-difluorophenyl)-3-n-butyryloxy-1,2-propanediol

A 200 ml reaction vessel was charged with 2 g of 2-(2,4-difluorophenyl)-1,3-di-n-butyryloxy-2-propanol, 100 mg of Lipase D made by Amano Pharmaceutical Co., Ltd. (derived from *Rhizopus delemer*, Enzyme No. 6) and 100 ml of 50 mM acetate buffer (pH 5). The resulting mixture was stirred at 30° C. to react for 18 hours. After the reaction liquid was extracted three times with 50 ml of ethyl acetate, the organic layers were combined and the combined organic layer was washed with saturated aqueous solution with sodium bicarbonate and with saturated aqueous solution with sodium chloride and further dried over anhydrous sodium sulfate. The solvent was removed under reduced pressure and the residue was purified by column chromatography on silica gel (eluent: n-hexane/ethyl acetate=3/2 ) to give 1.56 g of oily (R)-2-(2,4-difluorophenyl)-3-n-butyryloxy-1,2-propanediol. An optical purity thereof was determined in the same manner as Example 35. (Elution time: 16.6 minutes ((R)-form) and 12.9 minutes ((S)-form)).

$^1$H-NMR (400 MHz, CDCl$_3$) δ ppm: 7.67–7.64 (1H, m), 6.92–6.89 (1H, m), 6.82–6.77 (1H, m), 4.58–4.51 (2H, q), 4.02 (1H, s), 3.98–3.95 (1H, d), 3.79–3.76 (1H, d), 2.36 (1H, s), 2.23–2.19 (2H, m), 1.54–1.48 (2H, q), 0.84–0.81 (3H, t) $[α]_D^{25}$=–7.02° (C=0.997, CH$_3$OH) Optical purity: 86.4% ee

EXAMPLE 39

Synthesis of (R)-2-(2,4-difluorophenyl)-3-n-pentanoyloxy-1,2-propanediol

A 200 ml reaction vessel was charged with 2 g of 2-(2,4-difluorophenyl)-1,3-di-n-pentanoyloxy-2-propanol, 100 mg of Lipase D made by Amano Pharmaceutical Co., Ltd. (derived from *Rhizopus delemer*, Enzyme No. 6) and 100 ml of 50 mM acetate buffer (pH 5). The resulting mixture was stirred at 30° C. to react for 18 hours. After the reaction liquid was extracted three times with 50 ml of ethyl acetate, the organic layers were combined and the combined organic layer was washed with saturated aqueous solution with sodium bicarbonate and with saturated aqueous solution with sodium chloride and further dried over anhydrous sodium sulfate. The solvent was removed under reduced pressure and the residue was purified by column chromatography on silica gel (eluent: n-hexane/ethyl acetate=3/2) to give 1.01 g of oily (R)-2-(2,4-difluorophenyl)-3-n-pentanoyloxy-1,2-propanediol. An optical purity thereof was determined in the same manner as Example 35. (Elution time: 13.7 minutes ((R)-form) and 11.1 minutes ((S)-form)).

$^1$H-NMR (400 MHz, CDCl$_3$) δ ppm: 7.67–7.64 (1H, m), 6.93–6.89 (1H, m), 6.83–6.77 (1H, m), 4.58–4.51 (2H, q), 4.05 (1H, s), 3.98–3.95 (1H, d), 3.77–3.76 (1H, d), 2.35 (1H, s), 2.25–2.21 (2H, t), 1.47–1.43 (2H, t), 1.23–1.19 (2H, q), 0.85–0.82 (3H, t) $[α]_D^{25}$=–6.28° (C=0.987, CH$_3$OH) Optical purity: 92.1% ee

EXAMPLE 40

Synthesis of (R)-2-(2,4-difluorophenyl)-3-isobutyryloxy-1,2-propanediol

A 200 ml reaction vessel was charged with 2 g of 2-(2,4-difluorophenyl)-1,3-diisobutyryloxy-2-propanol, 100 mg of Lipase D made by Amano Pharmaceutical Co., Ltd. (derived from *Rhizopus delemer*, Enzyme No. 6), 90 ml of 50 mM acetate buffer (pH 5 ) and 10 ml of cyclohexane. The resulting mixture was stirred at 30° C. to react for 18 hours. After the reaction liquid was extracted three times with 50 ml of ethyl acetate, the organic layers were combined and the combined organic layer was washed with saturated aqueous solution with sodium bicarbonate and with saturated aqueous solution with sodium chloride and further dried over anhydrous sodium sulfate. The solvent was removed under reduced pressure and the residue was purified by means of column chromatography on silica gel (eluent: n-hexane/ethyl acetate=3/2) to give 1.51 g of oily (R)-2-(2,4-difluorophenyl)-3-isobutyryloxy-1,2-propanediol. An optical purity thereof was determined in the same manner as Example 35.

$^1$H-NMR (400 MHz, CDCl$_3$) δ ppm: 7.69–7.66 (1H, m), 6.91–6.87 (1H, m), 6.78–6.77 (1H, m), 4.54–4.45 (3H, m), 3.97–3.78 (2H, dd), 2.49–2.42 (1H, m), 1.01–0.99 (6H, m) $[α]_D^{25}$=7.04° (C=1.00, CH$_3$OH) Optical purity: 96.1% ee

EXAMPLE 41

Synthesis of (S)-2-(2,4-difluorophenyl)-1-propionyloxy-3-methanesulfonyloxy-2-propanol Into a solution wherein 0.5 g (R)-2-(2,4-difluorophenyl)-3-propionyloxy-1,2-propanediol obtained in Example 37 was dissolved in 5 ml of ethyl acetate was added dropwise 0.66 g of methanesulfonyl chloride at a temperature of 0° to 5° C., and thereto was added dropwise 0.46 g of pyridine at a temperature of 0° to 5° C. After dropping, the resulting liquid was stirred at room temperature for 16 hours. To the reaction mixture was added 20 ml of 1N hydrochloric acid and an organic layer separated. The organic layer was washed with saturated aqueous solution with sodium hydrogencarbonate and with saturated aqueous solution with sodium chloride, and dried over anhydrous sodium sulfate. The solvent was removed under reduced pressure and the residue was purified by column chromatography on silica gel (eluent: n-hexane/ethyl acetate=1/1) to give 0.53 g of oily (S)-2-(2,4-difluorophenyl)-1-propionyloxy-3-methanesulfonyloxy-2-propanol. An optical purity thereof was determined in the same manner as in Example 35. (Elution time: 24.3 minutes ((R)-form) and 26.9 minutes ((S)-form)).

$^1$H-NMR (400 MHz, CDCl$_3$) δ ppm: 7.73–7.67 (1H, m), 6.97–6.93 (1H, m), 6.84–6.81 (1H, m), 4.60–4.46 (4H, dd), 3.03 (3H, s), 2.32–2.26 (2H, q), 1.07–1.03 (3H, t) $[α]_D^{25}$=−8.04° (C=1.008, CH$_3$OH) Optical purity: 83.5% ee

EXAMPLE 42

Synthesis of (S)-2-(2,4-difluorophenyl)-1-n-butyryloxy-3-methanesulfonyloxy-2-propanol Into a solution wherein 0.3 g of (R)-2-(2,4-difluorophenyl)-3-n-butyryloxy-1,2-propanediol obtained in Example 38 was dissolved in 3 ml of ethyl acetate was added dropwise 374 mg of methanesulfonyl chloride at a temperature of 0° to 5° C., and thereto was added dropwise 260 mg of pyridine at a temperature of 0° to 5° C. After dropping, the resulting liquid was stirred at room temperature for 16 hours. To the reaction mixture was added 10 ml of 1N hydrochloric acid and an organic layer separated. The organic layer was washed with saturated aqueous solution with sodium hydrogencarbonate and with saturated aqueous solution with sodium chloride, and dried over anhydrous sodium sulfate. The solvent was removed under reduced pressure and the residue was purified by column chromatography on silica gel (eluent: n-hexane/ethyl acetate=1/1) to give 0.35 g of oily (S)-2-(2,4-difluorophenyl)-1-n-butyryloxy-3-methanesulfonyloxy-2-propanol. An optical purity thereof was determined in the same manner as in Example 35. (Elution time: 21.9 minutes ((R)-form) and 23.8 minutes ((S)-form)).

$^1$H-NMR (400 MHz, CDCl$_3$) δ ppm: 7.73–7.67 (1H, m), 6.97–6.92 (1H, m), 6.86–6.80 (1H, m), 4.58–4.48 (4H, q), 3.92 (1H, s), 3.04 (3H, s), 2.26–2.23 (2H, m), 1.57–1.51 (2H, q), 0.87–0.84 (3H, t) $[α]_D^{25}$=−9.07° (C=0.937, CH$_3$OH) Optical purity: 85.2% ee

EXAMPLE 43

Synthesis of (S)-2-(2,4-difluorophenyl)-1-n-pentanolyloxy-3-methanesulfonyloxy-2-propanol Into a solution wherein 0.3 g of (R)-2-(2,4-difluorophenyl)-3-n-pentanolyloxy-1,2-propanediol obtained in Example 39 was dissolved in 3 ml of ethyl acetate was added dropwise 356 mg of methanesulfonyl chloride at a temperature of 0° to 5° C., and thereto was added dropwise 247 mg of pyridine at a temperature of 0° to 5° C. After dropping, the resulting liquid was stirred at room temperature for 16 hours. To the reaction mixture was added 10 ml of 1N hydrochloric acid and an organic layer separated. The organic layer was washed with saturated aqueous solution with sodium hydrogencarbonate and with saturated aqueous solution with sodium chloride, and dried over anhydrous sodium sulfate. The solvent was removed under reduced pressure and the residue was purified by column chromatography on silica gel (eluent: n-hexane/ethyl acetate=1/1) to give 0.31 g of oily (S)-2-(2,4-difluorophenyl)-1-n-pentanolyloxy-3-methanesulfonyloxy-2-propanol. An optical purity thereof was determined in the same manner as in Example 35. (Elution time: 19.1 minutes ((R)-form) and 21.1 minutes ((S)-form)).

$^1$H-NMR (400 MHz, CDCl$_3$) δ ppm: 7.71–7.68 (1H, m), 6.96–6.93 (1H, m), 6.86–6.80 (1H, m), 4.57–4.48 (4H, q), 3.68 (1H, s), 3.04 (1H, s), 2.28–2.24 (2H, t), 1.50–1.46 (2H, t), 1.25–1.20 (2H, q), 0.87–0.83 (3H, t) $[α]_D^{25}$=−7.50° (C=0.960, CH$_3$OH) Optical purity: 91.0% ee

EXAMPLE 44

Synthesis of (S)-2-(2,4-difluorophenyl)-1-isobutyryloxy-3-methanesulfonyloxy-2-propanol Into a solution wherein 12 g of (R)-2-(2,4-difluorophenyl)-3-isobutyryloxy-1,2-propanediol obtained in Example 40 was dissolved in 120 ml of ethyl acetate was added dropwise 10 g of methanesulfonyl chloride at a temperature of 0° to 5° C., and thereto was added dropwise 6.92 g of pyridine at a temperature of 0° to 5° C. After dropping, the resulting liquid was stirred at room temperature for 16 hours. To the reaction mixture was added 400 ml of 1N hydrochloric acid and an organic layer separated. The organic layer was washed with saturated aqueous solution with sodium hydrogencarbonate and with saturated aqueous solution with sodium chloride, and dried over anhydrous sodium sulfate. The solvent was removed trader reduced pressure and the residue was purified by column chromatography on silica gel (eluent: n-hexane/ethyl acetate=1/1) to give 15.2 g of oily (S)-2-(2,4-difluorophenyl)-1-isobutyryloxy-3-methanesulfonyloxy-2-propanol. An optical purity thereof was determined in the same manner as in Example 35. (Elution time: 22.5 minutes ((R)-form) and 24.7 minutes ((S)-form)). $^1$H-NMR (400 MHz, CDCl$_3$) δ ppm: 7.71–7.68 (1H, m), 6.96–6.92 (1H, m), 6.85–6.81 (1H, m), 4.59–4.47 (4H, m), 3.04 (3H, s), 2.51–2.48 (1H, m), 1.06–1.04 (6H, m) Optical purity: 96.0% ee

EXAMPLE 45

Synthesis of (S)-2-(2,4-difluorophenyl)-2,3-epoxy-1-propanol

In 14 ml of methanol was dissolved 4.06 g of (S)-2-(2,4-difluorophenyl)-1-isobutyryloxy-3-methane-sulfonyloxy- 2-propanol obtained in Example 44. After a temperature of the resulting liquid was kept at 5° C., 14 ml of aqueous solution of 2N sodium m hydroxide was added dropwise thereto with cooling at 15° C. or below. After dropping, the resulting liquid was stirred at a temperature of 10° to 15° C. for 2 hours. Thereto 1N hydrochloric acid was added until the liquid was adjusted to pH 7 and methanol was removed under reduced pressure. To the residue was added ethyl acetate to extract. The resulting organic layer was washed with saturated aqueous solution with sodium chloride. The solvent was removed under reduced pressure and the residue was purified by column chromatography on silica gel (eluent: n-hexane/ethyl acetate=1/1) to give 2.04 g of oily (S)-2-(2,4-difluorophenyl)-2,3-epoxy-1-propanol. An optical purity thereof was determined in the same manner as in Example 35. (Elution time: 9.24 minutes ((S)-form) and 10.7 minutes ((R)-form)).

Optical purity: 96.0% ee

EXAMPLE 46

Synthesis of (R)-2-(2,4-difluorophenyl)-3-(1H-1,2, 4-triazole-1-yl)propane-1,2-diol In 10 ml of methanol was dissolved 8.8 g of (S)-2-(2,4-difluorophenyl)-1-isobutyryloxy-3-methane-sulfonyloxy-2-propanol obtained in Example 44 and thereto 7.95 g of sodium carbonate and 3.45 g of 1,2,4-triazole were added and allowed to reflux for 5 hours. After methanol was removed under reduced pressure, the residue was extracted with ethyl acetate to give oily substance. Thereto was added water and the resulting crystal was collected. The crystal was further recrystallized from acetonitrile to give 3.65 g (R)-2-(2,4-difluorophenyl)-3-(1H,1,2,4-triazole-1-yl) propane-1,2-diol. An optical purity thereof was determined in the same manner as in Example 35. (Elution time: 38.9 minutes ((S)-form) and 44.4 minutes ((R)-form)).

$^1$H-NMR (400 MHz, DMSO-$d_6$) ppm: 8.29 (1H, s), 7.70 (1H, s), 7.40–7.84 (1H, m), 7.14–7.12 (1H, t), 6.95–6.91 (1H, t), 5.77 (1H, s), 5.11–5.08 (1H, t), 4.57 (2H, s), 8.68–8.62 (2H, m) $[\alpha]_D^{25}$=–72.90° (C=1.015, $CH_3OH$)
Optical purity: 100% ee

EXAMPLE 47

Six 100 ml reaction vessels were prepared, each of which was charged with 5 g of 2-(2,4-difluorophenyl)-1,3-diisobutyryloxy-2-propanol, 45 ml of water, 5 ml of methylcyclohexane and 500 mg of Lipase D made by Amano Pharmaceutical Co., Ltd. (derived from *Rizopus delemter*, Enzyme No. 6). Each temperature of the vessles was kept at 15°, 20°, 25°, 30°, 35° and 40° C., respectively. Each of the resulting mixture was adjusted to pH 5 by controlling with sodium hydrate and allowed to react for 48 hours. After the reaction, each reaction mixture was extracted with ethyl acetate and each organic layer was washed with saturated aqueous solution with sodium hydrogencarbonate and with saturated aqueous solution with sodium chloride. The organic layer was dried over anhydrous sodium sulfate and the solvent was removed under reduced pressure. The residue was dissolved in methanol and HPLC analysis was carried out in the same manner as in Example 35. Each ratio of the formed (R)-2-(2,4-difluorophenyl)-3-isobutyryloxy-1,2-propanediol (monoester), 2-(2,4-difluorophenyl)-1,2,3-propanetriol (triol) and the residual substrate (diester) and an optical purity of the formed monoester were shown in Table 8.

TABLE 8

| Reaction temperature (°C.) | Diester (%) | Monoester (%) | Monoester (% ee) | Triol (%) |
| --- | --- | --- | --- | --- |
| 15 | 8.75 | 87.37 | 98.23 | 3.88 |
| 20 | 7.35 | 85.41 | 97.32 | 7.24 |
| 25 | 7.30 | 86.80 | 97.67 | 5.90 |
| 30 | 11.39 | 82.91 | 95.26 | 5.71 |
| 35 | 12.86 | 82.36 | 94.53 | 4.78 |
| 40 | 35.01 | 62.06 | 86.49 | 2.94 |

EXAMPLE 48

Three 100 ml reaction vessels were prepared, each of which was charnged with 5 g of 2-(2,4-difluorophenyl)-1,3-diisobutyryloxy-2-propanol, 45 ml of water, 5 ml of methylcyclohexane and Lipase D made by Amano Pharmaceutical Co., Ltd. (derived from *Rizopus delemter*, Enzyme No. 6). Each temperature of the vessels was kept at 6°, 10° and 15° C., respectively. Each of the resulting mixture was adjusted to pH 5.5 by controlling with sodium hydrate and allowed to react for 48 hours. After the reaction, each reaction mixture was extracted with ethyl acetate and each organic layer was washed with saturated aqueous solution with sodium hydrogencarbonate and with saturated aqueous solution with sodium chloride. The organic layer was dried over anhydrous sodium sulfate and the solvent was removed under reduced pressure. The residue was dissolved in methanol and HPLC analysis was carried out in the same manner as in Example 35. Each ratio of the formed (R)-2-(2,4-difluorophenyl)-3-isobutyryloxy-1,2-propanediol (monoester), 2-(2,4-difluorophenyl)-1,2,3-propanetriol (triol) and the residual substrate (diester) and an optical purity of the formed monoester were shown in Table 9.

TABLE 9

| Reaction temperature (°C.) | Diester (%) | Monoester (%) | Monoester (% ee) | Triol (%) |
| --- | --- | --- | --- | --- |
| 6 | 17.59 | 80.25 | 96.72 | 2.16 |
| 10 | 6.35 | 89.84 | 97.26 | 3.61 |
| 15 | 4.94 | 89.32 | 97.27 | 5.74 |

EXAMPLE 49

Stability of monoester (acetoxy form) to pH

Each test tube equipped with a closure was charged with 20 mg of (R)-2-(2,4-difluorophenyl)-3-acetoxy-1,2-propanediol (67.6% ee) and 1 ml of 100 mM each kind of buffer having a pH of 4 to 9 was added thereto and each test tube was shaken at 30° C. for 18 hours. Thereto was added 3 ml of ethyl acetate to extract and the solvent was removed under reduced pressure. The residue was dissolved in methanol and HPLC analysis was carried out in the same manner as in Example 35. An optical purity (R)-2-(2,4-difluorophenyl)-3-acetoxy-1,2-propanediol and a ratio of the formed 2-(2, 4-difluorophenyl)-1,2,3-propanetriol (triol) were shown in Table 10. (Eluent time: 14.9 minutes ((S)-monoester), 16.5 minutes ((R)-monoester) and 22.0 minutes (triol).

TABLE 10

| pH (Buffer) | Monoester (% ee) | Triol (%) |
|---|---|---|
| pH 4 (Acetate Buffer) | 65.0 | 0.28 |
| pH 5 (Acetate Buffer) | 61.8 | 0.22 |
| pH 6 (Phosphate Buffer) | 36.6 | 1.42 |
| pH 7 (Phosphate Buffer) | 1.2 | 12.1 |
| pH 8 (Phosphate Buffer) | 0.4 | 32.4 |
| pH 9 (Phosphate Buffer) | 1.6 | 9.8 |

EXAMPLE 50

Stability of monoester (isobutyryloxy form) to pH

Each test tube equipped with a closure was charged with 20 mg of (R)-2-(2,4-difluorophenyl)-3-isobutyryloxy-1,2-propanediol (46.2% ee) and 1 ml of 100 mM each kind of buffer having a pH of 4 to 9 was added thereto and each test tube was shaken at 30° C. for 18 hours. Thereto was added 3 ml of ethyl acetate to extract and the solvent was removed under reduced pressure. The residue was dissolved in methanol and HPLC analysis was carried out in the same manner as in Example 35. An optical purity (R)-2-(2,4-difluorophenyl)-3-isobutyryloxy-1,2-propanediol (monoester) and a ratio of the formed 2-(2,4-difluorophenyl)-1,2,3-propanetriol (triol) were shown in Table 11.

TABLE 11

| pH (Buffer) | Monoester (% ee) | Triol (%) |
|---|---|---|
| pH 4 (Acetate Buffer) | 46.0 | N.D. |
| pH 5 (Acetate Buffer) | 45.4 | N.D. |
| pH 6 (Phosphate Buffer) | 43.6 | N.D. |
| pH 7 (Phosphate Buffer) | 21.4 | 0.17 |
| pH 8 (Phosphate Buffer) | 2.6 | 0.80 |
| pH 9 (Phosphate Buffer) | 0.6 | 1.38 |

EXAMPLE 51

Synthesis of (−)-2-phenyl-1,3-isobutyryloxy-1,2-propanediol

A 100 ml reaction vessel was charged with 1 g of 2-phenyl-1,3-diisobutyryloxy-2-propanol, 100 mg of Lipase D made by Amano Pharmaceutical Co., Ltd. (derived from *Rizopus delemer*, Enzyme No. 6), 45 ml of 50 mM acetate buffer (pH 5) and 5 ml of cyclohexane and the mixture was stirred at 30° C. and allowed to react for 5 hours. After the resulting liquid was extracted three times with 50 ml of ethyl acetate, the organic layers were combined and washed with saturated aqueous solution with sodium hydrogencarbonate and with saturated aqueous solution with sodium chloride and dried over anhydrous sodium sulfate. The solvent was removed under reduced pressure and the residue was purified by column chromatography on silica gel (elution: n-hexane/ethyl acetate=1/1) to give 0.17 g of oily (−)-2-phenyl-1,3-isobutyryloxy-1,2-propanediol. An optical purity thereof was determined in the same manner as in Example 35. (Elution time: 19.3 minutes ((+)-form) and 27.6 minutes ((−)-form)).

$^1$H-NMR (400 MHz, CDCl$_3$) δ ppm: 7.48–7.46 (2H, m), 7.39–7.37 (2H, m), 7.35–7.28 (1H, m), 4.51–4.35 (2H, dd), 3.83–3.72 (2H, m), 3.38 (1H, s), 2.56–2.49 (1H, m), 1.71 (1H, s), 1.09–1.06 (6H, m) $[\alpha]_D^{25}$=−13.99° (C=1.00, CH$_3$OH) Optical purity: 93.7% ee

EXAMPLES 52 TO 63

The same procedure as in Example 51 was repeated except that as a starting substance of diester a compound shown in Table 12 was employing instead of 2-phenyl-1,3-diisobutyryloxy-2-propanol to give a corresponding monoester. Each of a yield, a specific rotation, an optical purity and $^1$H-NMR of the resulting monoester were summarized in Tables 13 and 14, respectively.

TABLE 12

| | Starting Substance of Diester |
|---|---|
| Ex. 52 | 2-(4-Fluorophenyl)-1,3-diisobutyryloxy-2-propanol |
| Ex. 53 | 2-(4-Chlorophenyl)-1,3-diisobutyryloxy-2-propanol |
| Ex. 54 | 2-(4-Methylphenyl)-1,3-diisobutyryloxy-2-propanol |
| Ex. 55 | 2-(4-Methoxyphenyl)-1,3-diisobutyryloxy-2-propanol |
| Ex. 56 | 2-(4-Biphenyl)-1,3-diisobutyryloxy-2-propanol |
| Ex. 57 | 2-(4-t-Butylphenyl)-1,3-diisobutyryloxy-2-propanol |
| Ex. 58 | 2-(2-Chlorophenyl)-1,3-diisobutyryloxy-2-propanol |
| Ex. 59 | 2-(2-Methylphenyl)-1,3-diisobutyryloxy-2-propanol |
| Ex. 60 | 2-(2,4-Dichlorophenyl)-1,3-diisobutyryloxy-2-propanol |
| Ex. 61 | 2-(2,4-Dimethylphenyl)-1,3-diisobutyryloxy-2-propanol |
| Ex. 62 | 2-(1-Naphthyl)-1,3-diisobutyryloxy-2-propanol |
| Ex. 63 | 2-(2-Naphthyl)-1,3-diisobutyryloxy-2-propanol |

TABLE 13

| Ex. No. | Yeild (g) | Specific Rotation (CH$_3$OH) | Optical purity (% ee) | Elution time of (+)-form/(−)-form (min.) |
|---|---|---|---|---|
| 52 | 0.71 | −10.6 (c = 1.000) | 95.3 | 21.5/23.2 |
| 53 | 0.68 | −9.52 (c = 0.987) | 95.7 | 23.7/24.6 |
| 54 | 0.49 | −0.49 (c = 0.934) | 93.8 | 21.4/31.2 |
| 55 | 0.52 | −9.01 (c = 0.976) | 78.4 | 33.8/45.3 |
| 56 | 0.59 | −7.46 (c = 0.938) | 91.1 | 49.2/42.6 |
| 57 | 0.55 | −9.83 (c = 0.935) | 96.9 | 13.7/11.6 |
| 58 | 0.64 | −8.87 (c = 0.947) | 80.0 | 12.4/22.1 |
| 59 | 0.16 | −5.77 (c = 0.970) | 83.8 | 12.3/19.0 |
| 60 | 0.11 | −8.60 (c = 0.976) | 75.4 | 12.9/15.5 |
| 61 | 0.063 | −3.42 (c = 0.934) | 89.7 | 11.8/17.6 |
| 62 | 0.61 | −12.8 (c = 0.923) | 58.0 | 25.2/21.8 |
| 63 | 0.66 | −5.41 (c = 0.924) | 97.6 | 32.0/33.9 |

TABLE 14

| Ex. No. | $^1$H-NMR (400 MHz, CDCl$_3$) δ ppm |
|---|---|
| 52 | 7.47–7.42(2H, m), 7.08–7.03(2H, m), 4.48–4.33(2H, dd), 3.80–3.68(2H, m), 3.47(1H, s), 2.56–2.49(1H, m), 1.78 (1H, s), 1.09–1.07(6H, m) |
| 53 | 7.43–7.33(4H, dd), 4.48–4.33(2H, dd), 3.79–3.67(2H, m), 3.42(1H, s), 2.56–2.49(1H, m), 1.67(1H, s), 1.10–1.08(6H, m) |
| 54 | 7.36–7.17(4H, dd), 4.48–4.32(2H, dd), 3.80–3.71(2H, m), 3.31(1H, s), 2.56–2.49(1H, m), 2.34(3H, s), 1.75(1H, s), 1.11–1.08(6H, m) |
| 55 | 7.40–6.88(4H, dd), 4.48–4.32(2H, dd), 3.81(3H, s), 3.79–3.70(2H, m), 3.27(1H, s), 2.57–2.50(1H, m), 2.34 (1H, s), 1.11–1.09(6H, m) |
| 56 | 7.62–7.53(6H, m), 7.46–7.42(2H, m), 7.37–7.34(1H, m), 4.55–4.39(2H, dd), 3.87–3.77(2H, m), 3.37(1H, s), 2.59–2.52(1H, m), 1.62(1H, s), 1.12–1.09(6H, m) |
| 57 | 7.39(4H, m), 4.51–4.33(2H, dd), 3.82–3.74(2H, m), 3.23(1H, s), 2.57–2.50(1H, m), 2.25(1H, s), 1.31(9H, s), 1.10–1.08(6H, m) |
| 58 | 7.81–7.79(1H, m), 7.36–7.34(1H, m), 7.37–7.23(2H, m), 4.93–4.67(2H, dd), 4.46(1H, s), 4.21–3.94(2H, dd), 2.45–2.36(1H, m), 0.96–0.88(6H, m) |
| 59 | 7.45–7.43(1H, m), 7.21–7.15(3H, m), 4.64–4.50(2H, dd), 3.93–3.84(2H, m), 3.68(1H, s), 2.55(3H, s), 2.51–2.44(1H, m), 1.04–0.99(6H, m), 2.45–2.36(1H, m), 0.96–0.88(6H, m) |
| 60 | 7.78–7.76(1H, d), 7.38(1H, d), 7.29–7.26(1H, m), 4.89–4.66 (2H, dd), 4.48(1H, s), 4.18–4.09(1H, m), 3.92–3.04(1H, m), 2.38–2.32(1H, m), 1.66(1H, m), 0.99–0.92(6H, m) |
| 61 | 7.32–7.30(1H, d), 6.99–6.97(1H, d), 4.61–4.47(2H, dd), 3.90–3.84(2H, m), 2.55–2.46(1H, m), 2.51(3H, s), 2.29(3H, s), 1.07–1.02(6H, m) |

TABLE 14-continued

| Ex. No. | ¹H-NMR (400 MHz, CDCl₃) δ ppm |
|---|---|
| 62 | 8.67–8.65(1H, d), 7.88–7.81(2H, m), 7.61–7.59(1H, m), 7.54–7.41(3H, m), 4.87–4.70(2H, dd), 4.16–4.09(H, m), 3.70(1H, s), 2.52–2.47(1H, m), 1.58(1H, s), 1.28–1.24(1H, m), |
| 63 | 7.97–7.53(1H, m), 7.85–7.81(2H, m), 7.55–7.53(1H, m), 7.50–7.46(3H, m), 4.59–4.45(2H, dd), 3.90–3.81(2H, m), 3.55 (1H, s), 2.54–2.47(1H, m), 1.27–1.22(1H, m), 1.07–1.04(5H, m) |

EXAMPLE 64

Synthesis of (S)-2-(2,4-difluorophenyl)-1-isobutyryloxy-3-(4-methylphenyl)sulfonyloxy-2-propanol Into a solution wherein 1 g of (R)-2-(2,4-difluorophenyl)-3-isobutyryloxy-1,2-propanediol obtained in Example 40 was dissolved in 2 ml of ethyl acetate was added dropwise 1 ml of tetrahydrofuran wherein 1.26 g p-toluenesulfonyl acid chloride was dissolved at a temperature of 0° to 5° C., and furthermore, thereto was added dropwise 0.52 g of pyridine at a temperature of 0° to 5° C. After the dropping, the resulting mixture was stirred at room temperature for 16 hours. To thus obtained liquid was added 10 ml of 1N hydrochloric acid and the liquid was subject to a separation. The organic layer was washed with saturated aqueous solution with sodium hydrogencarbonate and with saturated aqueous solution with sodium chloride, and dried over anhydrous sodium sulfate. The solvent was removed under reduced pressure and the residue was purified by column chromatography on silica gel (eluent: n-hexane/ethyl acetate=5/2) to give 1.4 g of oily (S)-2-(2,4-difluorophenyl)-1-isobutyryloxy-3-(4-methylphenyl)sulfonyloxy-2-propanol. An optical purity thereof was determined in the same manner as in Example 35. (Elution time: 23.1 minutes ((R)-form) and 33.7 minutes ((S)-form)).

¹H-NMR (400 MHz, CDCl₃) δ ppm: 7.72–7.40 (2H, d), 7.66–7.59 (1H, m), 7.33–7.31 (2H, d), 6.91–6.86 (1H, m), 6.73–6.68 (1H, m), 4.51–4.25 (4H, m), 3.72 (1H, s), 2.45 (3H, s), 2.49–2.42 (1H, m), 1.03–0.99 (6H, m) Optical purity: 95.6% ee

EXAMPLE 65

Synthesis of 1,3-dichloroacetoxy-2-(2,4-difluorophenyl)-2-propanol (according to Reaction formula 2)

In 30 ml dichloromethane were dissolved 3.06 g of 2-(2,4-difluorophenyl)-1,2,3-propanetriol and 3.79 g of triethylamine and thereto was added dropwise 3.73 g of chloroacetyl chloride at a temperature of −10° C. or below and after the dropping, allowed to react at room temperature for 4 hours. Into the reaction liquid were added 10 ml of water and 100 ml of ethyl acetate, and an organic layer was separated. The organic layer was washed with 1N hydrochloric acid, and further with water and with saturated aqueous solution with sodium chloride. After the organic layer was dried over anhydrous sodium sulfate, the solvent was removed under reduced pressure. Thus obtained concentrate was purified by column chromatography on silica gel (hexane/ethyl acetate=2/1) to give 5.53 g of the oily desired compound.

¹H-NMR (400 MHz, CDCl₃) δ ppm:7.71–7.65 (1H, m), 6.97–6.95 (1H, m), 6.93–6.81 (1H, m), 4.65–4.55 (4H, dd), 4.05 (4H, s), 3.25 (1H, s)

EXAMPLE 66

Synthesis of (R)-2-(2,4-difluorophenyl)-3-(1H-1,2,4-triazole-1-yl)propane-1,2-diol In 16.8 ml of tetrahydrofuran was dissolved 18.2 g of (S)-2-(2,4-difluorophenyl)-2,3-epoxy-2-propanol obtained in Example 45 and thereto 20.3 g of potassium carbonate and 10.2 g of 1,2,4-triazole were added and allowed to reflux for 20 hours. The reaction mixture was cooled to room temperature and thereto were added 90 ml of water and 30 g of sodium chloride. The resulting liquid was extracted twice with 100 ml of ethyl acetate. The solvent was removed under reduced pressure and to the residue were added 80 ml of chloroform and 16 ml of n-hexane and the resulting liquid was stirred at room temperature for 20 hours. A deposited crystal was collected and was further recrystallized from acetonitrile. The resulting crystal was dried under reduced pressure to give 10.8 of (R)-2-(2,4-difluorophenyl)-3-(1H, 1,2,4-triazole-1-yl)propane-1,2-diol (optical purity: 100% ee).

INDUSTRIAL AVAILABILITY

According to the present invention, an optical active 2-arylglycerol derivative which is a novel and useful as a synthetic intermediate of medicament can be provided and furthermore, (R)-2-(2, 4-difluorophenyl)-3-(1H-1,2,4-triazole-1-yl)-propane-1,2-diol which is useful as an antifungal agent can be prepared.

We claim:

1. An optically active 2-aryl-3-acyloxy-1,2-propanediol compound represented by the formula (VIII):

(VIII)

wherein Ar is phenyl, 4-fluorophenyl, 4-chlorophenyl, 4-methylphenyl, 4-methoxyphenyl, 4-biphenyl, 4-tert-butylphenyl, 2-chlorophenyl, 2-methylphenyl, 2,4-dichlorophenyl, 2,4-dimethylphenyl, 1-naphthyl or 2-naphthyl, and R is ethyl, n-propyl, n-butyl, n-pentyl, n-hexyl, n-heptyl, isopropyl, isobutyl, chloromethyl, β-chloroethyl or γ-chloropropyl.

2. The compound of claim 1, wherein Ar is 4-fluorophenyl, 4-chlorophenyl, 2-chlorophenyl or 2,4-dichlorophenyl.

3. The compound of claim 1, wherein Ar is phenyl, 4-methylphenyl, 4-methoxyphenyl, 4-tert-butylphenyl, 2-methylphenyl or 2,4-dimethylphenyl.

4. The compound of claim 1, wherein Ar is 4-biphenyl, 1-naphthyl or 2-naphthyl.

5. The compound of claim 1 represented by the formula (VIIIb):

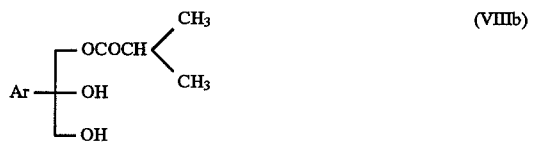

(VIIIb)

wherein Ar is phenyl, 4-fluorophenyl, 4-chlorophenyl, 4-methylphenyl, 4-methoxyphenyl, 4-biphenyl, 4-tert-butylphenyl, 2-chlorophenyl, 2-methylphenyl, 2,4-dichlorophenyl, 2,4-dimethylphenyl, 1-naphthyl or 2-naphthyl.

* * * * *